US012751705B2

(12) United States Patent
Miyasaka et al.

(10) Patent No.: US 12,751,705 B2
(45) Date of Patent: Oct. 6, 2026

(54) DEVICE AND METHOD FOR PROVIDING A VOLUME IN A LUMEN

(71) Applicant: Nanyang Technological University, Singapore (SG)

(72) Inventors: Muneaki Miyasaka, Singapore (SG); Jiajun Liu, Singapore (SG); Soo Jay Louis Phee, Singapore (SG)

(73) Assignee: Nanyang Technological University, Singapore (SG)

(*) Notice: Subject to any disclaimer, the term of this patent is extended or adjusted under 35 U.S.C. 154(b) by 573 days.

(21) Appl. No.: 18/277,031

(22) PCT Filed: Feb. 21, 2022

(86) PCT No.: PCT/SG2022/050081
§ 371 (c)(1),
(2) Date: Aug. 11, 2023

(87) PCT Pub. No.: WO2022/177510
PCT Pub. Date: Aug. 25, 2022

(65) Prior Publication Data

US 2024/0115250 A1 Apr. 11, 2024

(30) Foreign Application Priority Data

Feb. 22, 2021 (SG) ........................... 10202101738X

(51) Int. Cl.
*A61B 17/02* (2006.01)
*A61B 17/00* (2006.01)

(52) U.S. Cl.
CPC *A61B 17/0218* (2013.01); *A61B 2017/00367* (2013.01); *A61B 2017/0225* (2013.01)

(58) Field of Classification Search
CPC .... A61B 2017/0287; A61B 2017/0218; A61B 2017/0225; A61B 2017/00367; A61B 1/32; A61B 17/0218
See application file for complete search history.

(56) References Cited

U.S. PATENT DOCUMENTS

2002/0123766 A1 9/2002 Seguin et al.
2004/0097792 A1* 5/2004 Moll ...................... A61B 90/50 600/201

(Continued)

FOREIGN PATENT DOCUMENTS

CN 103654888 A * 3/2014 ......... A61B 17/0218

OTHER PUBLICATIONS

Miyasaka M. et al., Flexible and Deployable Colon Support Structure for Endoluminal Interventions. IEEE Access, Jun. 18, 2021, vol. 9, pp. 91754-91763 [Retrieved on May 19, 2022] <DOI: 10.1109/ACCESS.2021.3090411>.

(Continued)

*Primary Examiner* — Jan Christopher L Merene
(74) *Attorney, Agent, or Firm* — Tyler Sisk; Casimir Jones SC

(57) ABSTRACT

A device to provide a volume in a lumen for endoscopic procedures is provided. The device comprises a plurality of flexible tube linkages, said each flexible tube linkage having a distal end and a proximal end, an actuation and locking mechanism comprising an actuation wire, wherein the proximal end of the each flexible tube linkage is connected to the actuation and locking mechanism, wherein the actuation wire is connected about the distal of the each flexible tube linkage, and wherein the actuation wire is arranged to rotate relative to the actuation and locking mechanism so as to define the volume.

12 Claims, 29 Drawing Sheets

(56) References Cited

U.S. PATENT DOCUMENTS

| | | | | |
|---|---|---|---|---|
| 2006/0004261 | A1* | 1/2006 | Douglas | A61B 1/32 600/210 |
| 2007/0119461 | A1* | 5/2007 | Biancucci | A61B 17/12036 128/846 |
| 2010/0094327 | A1 | 4/2010 | Milsom et al. | |
| 2013/0123828 | A1* | 5/2013 | Culmer | A61B 17/0218 606/185 |
| 2013/0274553 | A1* | 10/2013 | Piskun | A61B 1/00154 600/114 |
| 2017/0252027 | A1 | 9/2017 | Kasic, II | |
| 2018/0014885 | A1 | 1/2018 | Zarrouk et al. | |
| 2020/0261095 | A1* | 8/2020 | Yi | A61B 17/1285 |
| 2020/0352431 | A1 | 11/2020 | Piskun | |
| 2025/0040922 | A1* | 2/2025 | Ruffieux | A61B 17/0469 |

OTHER PUBLICATIONS

China National Intellectual Property Administration, Office Action for CN Application No. 2022800152257, issued on May 14, 2026.

* cited by examiner

DEVICE AND METHOD FOR PROVIDING A VOLUME IN A LUMEN

PRIORITY CLAIM

This application is a national stage application of PCT/SG2022/050081, filed on 21 Feb. 2022, which claims priority from Singapore Application No. 10202101738X, filed on 22 Feb. 2021, the contents of which are hereby incorporated by reference in their entirety for all purposes.

TECHNICAL FIELD

The present invention generally relates to creating a worksite in a collapsible tube structure such as a lumen and, more particularly, relates to a device and a method for providing a volume in a lumen.

BACKGROUND OF THE DISCLOSURE

Working in collapsible conduits, particularly small collapsible conduits, is challenging as the walls tend to collapse in upon themselves making it difficult to maintain a volume within the conduit as a workspace. This is complicated when the conduit is very small, such as a body lumen, and when working within the conduit from a remote location outside the conduit.

An example of working within a small collapsible conduit from a remote location outside the conduit includes delivering a non-invasive scope into a lumen for visualization and instruments (i.e., graspers, cutters, cauterizing tools, ultrasound probes, etc.) for tissue manipulation.

In comparison to other bodily lumens, the gastrointestinal (GI) tract has a relatively large lumen. The evaluation and treatment of the GI tract are hampered by the regional and local anatomic geometry and surface condition of the colon. Furthermore, the colon is divided into various sections (ascending colon, transverse colon, descending colon, and sigmoid colon), each section with a regional turn and numerous folds in between. Additionally, the colon tissue is viscoelastic, and its condition varies based on its location.

The use of a conventional endoscope to fully visualize the walls of the colon is challenging due to these situations. When an endoscope is placed into the colon, the colon may constrict due to spasms and peristalsis. The constriction makes visibility more difficult and restricts access to the targeted tissues at a workspace for endoscope-inserted instruments.

Furthermore, during endoscopic procedures, the surrounding tissue in the GI tract may collapse as a result of the weight and intra-abdominal pressure (IAP) in the GI tract, obstructing vision and task space required to perform the operations appropriately.

Insufflation of the colon has been used to enable access to the targeted tissues while avoiding spasms and peristalsis. Gas insufflation is one form of insufflation, in which a gas like carbon dioxide is used to enlarge the lumen for better visualization and facilitating the advancement of the colonoscope. Carbon dioxide is a popular choice for insufflation because it is quickly absorbed into the bloodstream by the gastrointestinal mucosa and then exhaled into the lungs. However, utilizing carbon dioxide as an insufflation gas has significant drawbacks, such as post-procedure pain from abdominal distention and embolism. Furthermore, people with pre-existing medical problems such as chronic obstructive lung disease may be more susceptible to carbon dioxide retention. Additionally, perforation during endoscopic treatments, whether unintentional or intentional, permits insufflation gas to escape into the peritoneal cavity, making it harder to maintain the intra-luminal space and perhaps causing cardiac distress.

Therefore, there is a need to provide a device and method having the ability to expand a body lumen or soft collapsible conduit to expose and maintain a workspace such as creating a volume within sidewall tissue of a lumen for endoscopic diagnosis, therapy, and surgery without the need for insufflation. Having an expanded and stable intra-luminal space will provide proper visualization of a target area (e.g., target tissue) as well as surrounding sidewalls and create a volume within the soft collapsible conduit for a proper workspace to manipulate the delivery mechanism (e.g., an endoscope or catheter or similar flexible assembly) as well as tools or other instruments independently. Furthermore, other desirable features and characteristics will become apparent from the subsequent detailed description and the appended claims, taken in conjunction with the accompanying drawings and this background of the disclosure.

SUMMARY

According to at least one aspect of the present embodiments, a device to provide a volume in a lumen for endoscopic procedures is provided. The device comprises a plurality of flexible tube linkages, said each flexible tube linkage having a distal end and a proximal end, an actuation and locking mechanism comprising an actuation wire, wherein the proximal end of the each flexible tube linkage is connected to the actuation and locking mechanism, wherein the actuation wire is connected about the distal of the each flexible tube linkage, and wherein the actuation wire is arranged to rotate relative to the actuation and locking mechanism so as to define the volume.

According to other aspects of the present embodiments, a method for providing a volume in a lumen for endoscopic procedures. The method comprising the steps of advancing a device to a target site; and rotating the actuation and locking mechanism such that the distal ends of the plurality of flexible tube linkage are brought in close proximity to the proximal ends of the plurality of flexible tube linkages, thereby forming the defined volume.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with present embodiments.

FIGS. 10A and 10B are schematic views of a deployed lumen expansion device in accordance with the present embodiments, wherein FIG. 10A is a perspective view from a proximal side and FIG. 10B is a perspective view from a distal side.

Figure 1A:
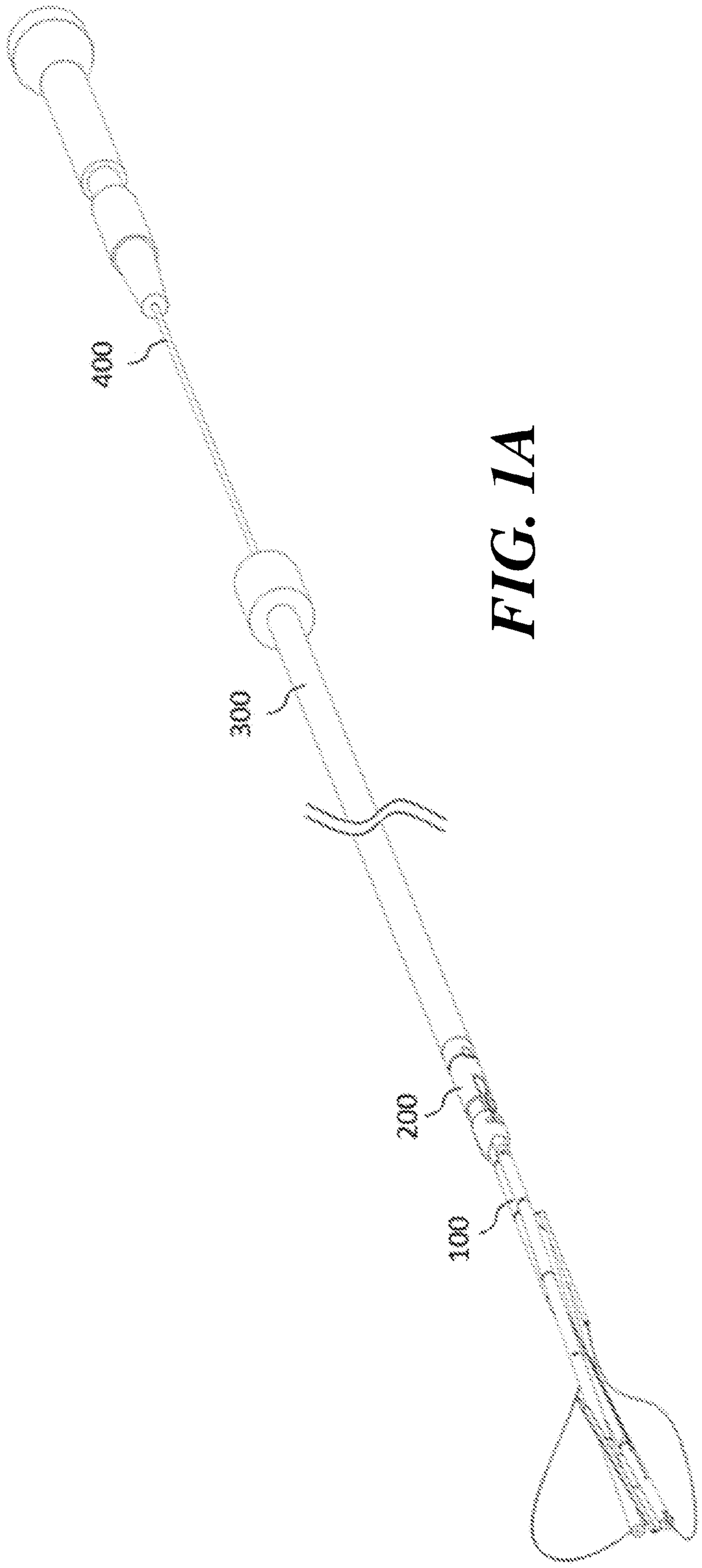
FIGS. 1A and 1B are perspective views of a body lumen expansion device in accordance with present embodiments.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of present embodiments to present a device and method for defining a structure to provide a volume in a collapsible tubular structure such as a lumen.

According to one embodiment of the present embodiment, the device comprises a flexible main structure, an actuation and lock mechanism, and delivery/manipulation tools. The flexible main structure comprises multiple flexible frames that can pop up from a closed collapsible structure to a three-dimensional (3D) structure to create a volume in a lumen for endoscopic procedures. Each flexible frame may be pre-shaped, or it may be a linkage with multiple revolution joints. The revolution joints may be created by notches (may be single or multiple notches for one joint) or pin-joints. The flexible frames are linked together to form the final 3D (three-dimensional) structure. The transformation of the flexible main structure is powered up by an external source and the final 3D structure is contained by activation of a locking mechanism. The flexible main structure may be completely detached from the delivery tools. After endoscopic procedures, the final 3D structure may be unlocked and the flexible main structure may be retrieved by manipulation tools. All parts are sufficiently flexible and/or small to pass inside an instrument channel of the endoscope.

According to another embodiment of the present invention, the flexible main structure/frame consists of two serial linkages with four revolution joints created by notches. The linkages are made out of high-strength and flexible material (i.e., PET or superelastic nitinol bars, rods, or tubes). The joints of one linkage are assigned to form a forward-left-up-diagonally right-down shape. On the other hand, another linkage is designed to form a shape/structure of forward-right-up-diagonally left-down. Those linkages are placed next to each other and linked with an elastic element (for example, wire or wire rope preferably made out of nitinol) to keep their proper relative positions. When all the joints are at their maximum limit, the linkages transform from a closed collapsible structure to a cuboid tent-like shape/structure. In addition, flexible bars, rods, or tubes may be added to strengthen the bottom face of the structure. Alternatively, the deployable shape/structure, i.e., the final 3D shape includes a triangular prism, a pyramid, a cylinder, a tent, and dome-like shapes or structures, depending on the number and length of linkages/frames and number, placement, and rotational limit of joints. The joint actuation is performed by tensioning of a line, where the line is a high strength, low stretch, and the flexible line includes superelastic nitinol wire or synthetic/metal wire rope, said line passing through the frame. As the line is pulled, the structure pops up while the tip of the frames is pulled toward the proximal side and the joints of the tent structure are forced to rotate to reach their limits.

According to another embodiment of the present invention, the actuation and lock mechanism consists of three components, an actuation base, an actuation rod, and a locking cap. The length of the line required to be pulled to transform from a closed collapsible shape to deployed tent shape is roughly as long as the length of the closed collapsible shape of the structure. In order to keep the device as short as possible, the actuation is triggered by winding the line. The distal end of the actuation base is connected to the flexible main structure. On a proximal end, the actuation base has a threaded hole in the middle grooves on the outer surface to guide the actuation line coming out of the flexible main structure. The ridges next to the grooves function as guides for the locking cap. The actuation rod has a screw on the distal end and a key right next to it. The screw fits the threaded hole on the actuation base and the actuation line is terminated at the key. A large portion of the screw is initially placed inside the threaded hole of the actuation base. As the screw is unscrewed, more thread is exposed while the actuation line is wound around it. The locking cap comprises a guide slot and key slots. After the device is fully deployed, the locking cap slid in along the ridges of the actuation base until the key on the actuation rod fits into one of the key slots to make the screw non-rotatable.

According to another embodiment of the present invention, the actuation and lock mechanism consists of two components, an L-socket actuation base, and a t-shaped lock. A distal end of the L-socket actuation base is connected to the flexible main structure. A line/wire goes through holes on the L-socket actuation base and the T-shaped lock. The line/wire is twisted by rotating a manipulation tool attached to the T-shaped lock. After twisting the line/wire, the T-shaped lock is pushed into the L-socket to avoid untwisting the line/wire. The friction generated by twisting prevents the line/wire from slacking and thus keeps the tension. Thus, pulling the line/wire in a linear motion causes the line to be twisted and in a locking configuration. Further, the dimension of the deployed device is shorter due to the twisting of the line/wire, and this allows the deployed device to go through narrow and sharp bends.

According to another embodiment of the present invention, tissues squeezing into a created space in the deployed structure are prevented from entering the created space by another loop of a line/wire intersecting the faces of the structure. While the proximal face of the structure is left open for the access of endoscope and instruments, the spacing of the tissue block lines/wires intersecting the other faces of the structure can be adjusted depending on the condition of the surrounding tissues and surgical requirements (i.e., type, size and condition of lesions). The tissue block line/wire also needs to be tensioned for holding tissues pressing in. This tensioning may be provided by terminating the line at the actuation rod and coupling it with the linear unscrewing motion. Alternatively, the tensioning may be performed using the same process of tensioning the actuation line/wire. In both cases, the actuation and lock mechanism keeps the tension of the actuation line/wire and tissue block line/wire after the deployment of the flexible main structure.

According to another embodiment of the present invention, all the manipulations of the device including delivery, deployment actuation, locking, detaching, tension release, and retraction will be performed with the manipulation tools through an endoscopic channel and manipulated at their proximal ends which are outside of the endoscope.

As a result of recent advancements in endoscopic techniques such as diagnostic and therapeutic endoscopy and Natural Orifice Transluminal Endoscopic Surgery (NOTES), new treatment approaches and procedures have been developed. The evaluation and treatment of the GI tract are hampered by the regional and local anatomic geometry and surface condition of the colon. Additionally, the colon tissue is viscoelastic, and its condition varies based on its location. The use of a conventional endoscope to fully visualize the walls of the colon is challenging due as the colon may constrict due to spasms and peristalsis making visibility more difficult and restricting access to targeted tissues at a workspace for endoscope-inserted instruments. Present embodiments provide a device and method to expand a body lumen to provide a workspace volume within the lumen during endoscopic diagnosis, therapy, and surgery.

Referring to FIG. 1A, an embodiment of the present invention comprises a flexible main structure 100, an actuation and lock mechanism 200, a manipulation tube 300 and a manipulation rod 400 in accordance with present embodiments. The flexible main structure 100 and the actuation and lock mechanism 200 are at a distal end of a flexible assembly such as an endoscopic device (e.g., endoscope), catheter or similar flexible assembly and can be delivered to a workspace within a lumen or similar soft collapsible conduit and controlled by a user via the manipulation tube 300 and the manipulation rod 400 at a proximal end of the flexible assembly.

Figure 1B:
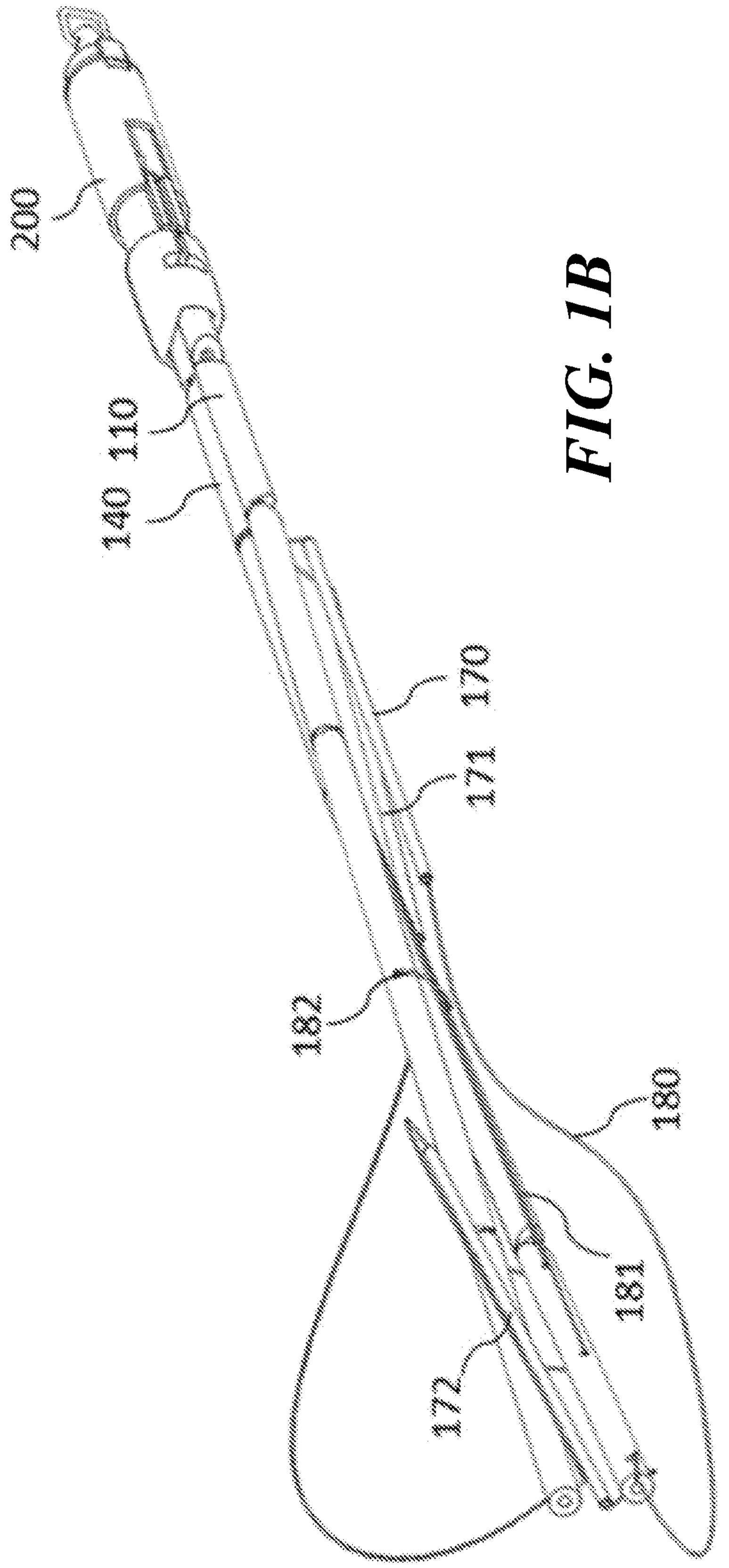

FIG. 1B shows the details of the flexible main structure 100 and the actuation and lock mechanism 200 in accordance with present embodiments. An actuation line 180 terminates at the actuation and lock mechanism 200, passing through a left flexible tube linkage 110, a right flexible tube linkage 140, side tube frames 170 and 171, and a distal tube 172. Each of the left and right flexible tube linkages 110, 140 includes a distal end and a proximal end, where the proximal ends of each of the left and right flexible tube linkages 110, 140 are connected to the actuation and locking mechanism 200, and wherein the distal end of the actuation line 180 is connected to the distal end of the left and right flexible tube linkages 110, 140. The distal tube 172 is coupled to at least one of the proximal ends of the left and right flexible tube linkages 110, 140. A tissue blocking wire 181 terminates at the actuation and lock mechanism 200, and the tissue blocking wire 181 passes through an inside and an outside of the left and right flexible tube linkages 110, 140. The left and right flexible tube linkages 110, 140 are joined with a flexible element 182 to constrain their relative positions. Alternatively, the flexible tube linkages may be a plurality of flexible tube linkages. Alternatively, the left and right flexible tube linkages may be a single structure. Alternatively, the flexible main structure 100, the actuation and lock mechanism 200, the manipulation tube 300 and the manipulation rod 400 may be coupled to form a single structure. In accordance with the present embodiments, the left flexible tube linkage 110, the right flexible tube linkage 140, the side tube frames 170 and 171, and the distal tube 172 comprise a closed collapsible structure which is delivered within the flexible main structure 100 to the workspace where the actuation line 180 is manipulated by the user at the proximal end of the flexible assembly to transform the closed collapsible structure to a 3D (three-dimensional) deployed structure for advantageously creating a workspace volume within the lumen or other small collapsible conduit.

Figure 2A:
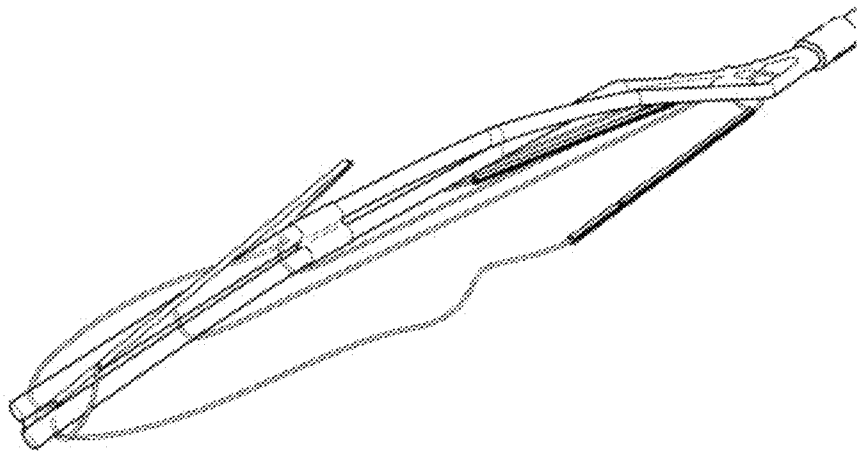
FIGS. 2A to 2D illustrate a deployment process of a flexible main structure of the lumen expansion device in accordance with the present embodiments.
Figure 2B:
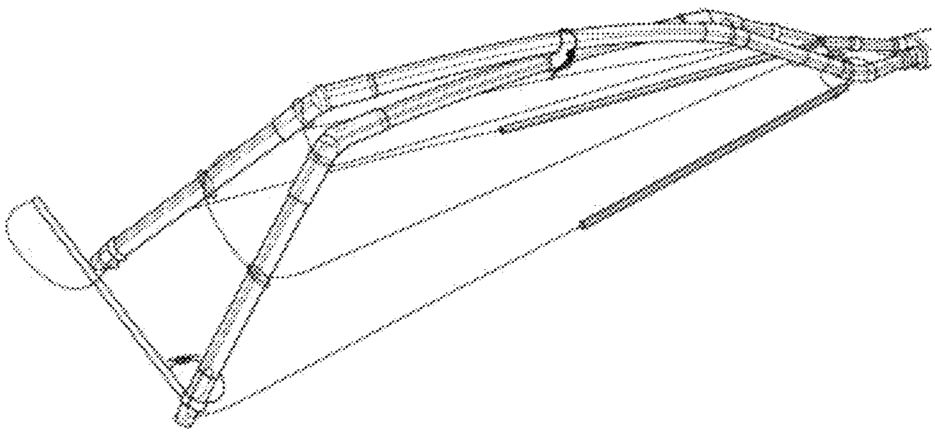
Figure 2C:
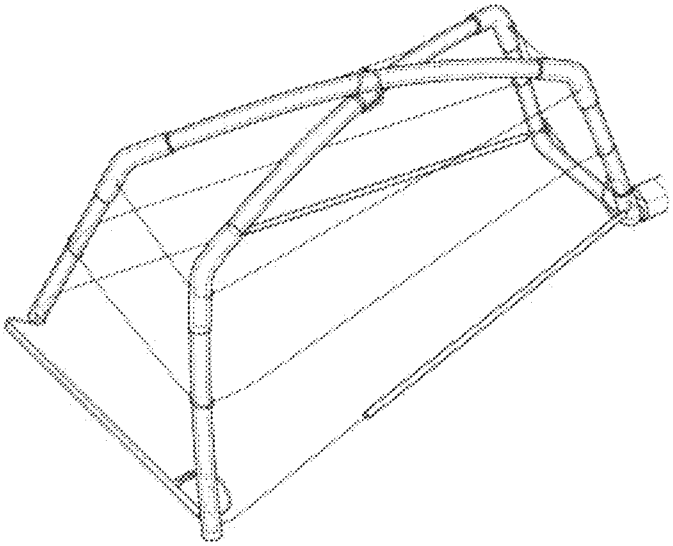
Figure 2D:
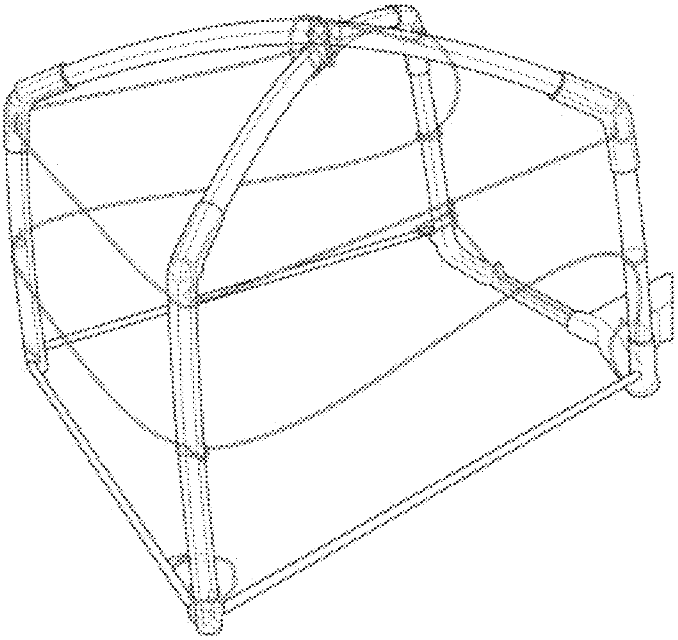

FIGS. 2A to 2D depict the flexible main structure 100 of the device at various steps (FIGS. 2A, 2B, 2C, 2D) during transformation from the closed collapsible structure to the three-dimensional (3D) deployed structure (FIG. 2D). The actuation and locking mechanism 200 is arranged to rotate relative to the left and right flexible tube linkages 100, 140 to pull a distal end of the actuation line 180 towards the actuation and locking mechanism 200 thereby moving the distal end of each of the left and right flexible tube linkages 100, 140 towards the proximal end of each of the left and right flexible tube linkages 100, 140 thereby creating a structure defined by each of the left and right flexible tube linkages 100, 140 which defines a volume. In the defined structure i.e., the 3D deployed configuration, the tissue blocking wire 181 is perpendicularly connected to the left and right flexible tube linkages 100, 140. When the actuation and locking mechanism 200 is rotated, tension increases to provide rigidity to the structure defined by each of the flexible tube linkages 110, 140 and by the side tube frames 170, 171 and the distal tube 172. Alternatively, the actuation line 180 may be an actuation wire, the tissue blocking lines 181 may be a structure wire, and the volume may be an intra-luminal space.

Figure 3A:
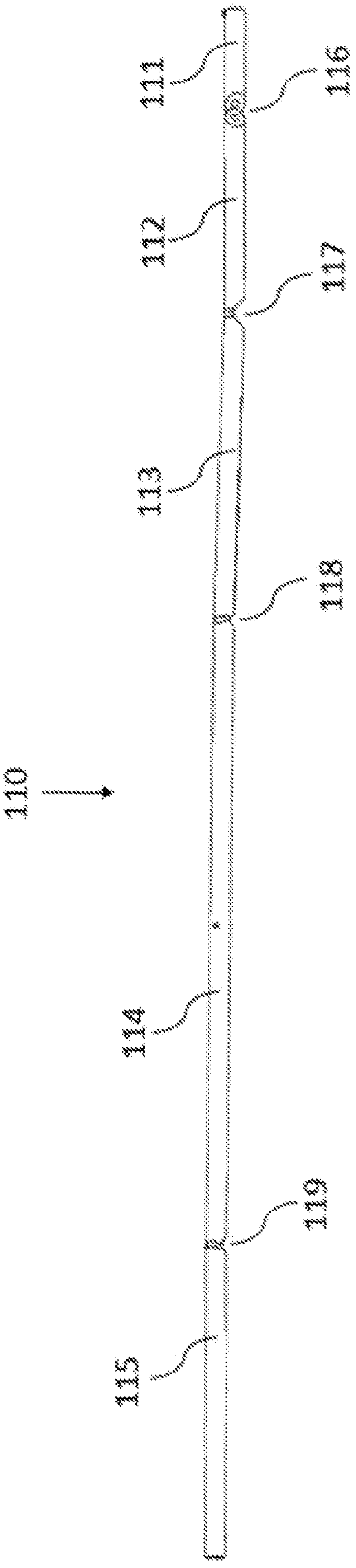
FIGS. 3A and 3B are left-side and right-side views of flexible tube linkages of the lumen expansion device in accordance with the present embodiments.
Figure 3B:
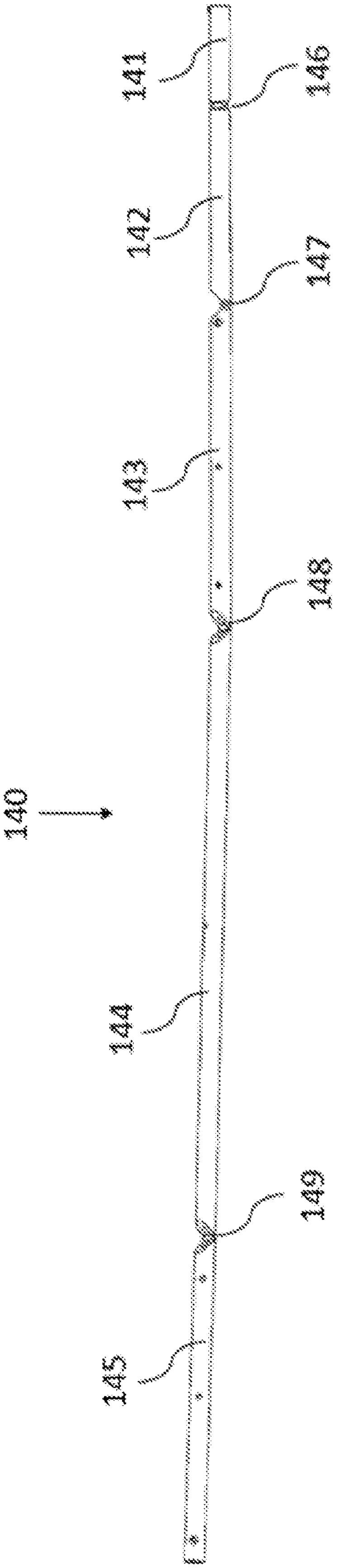

Referring to FIGS. 3A and 3B, both the left flexible tube linkage 110 and right flexible tube linkage 140 comprises five flexible linkages portions 111 to 115 and 141 to 145 and four rotating elements with hard stops 116 to 119 and 146 to 149 in accordance with the present embodiments. The hard stops may be provided by pin joints or notches, wherein each rotating element connects adjoining ones of the five linkage portions 111 to 115, 141 to 145. The orientations of the joints are assigned to be symmetric for the left and right flexible tube linkages 110, 140 to achieve the 3D shape/structure as shown in FIG. 2D after deployment. The design parameters may include the number and length of linkages/frames and the number of the joints, placement of the joints, and rotational limit of the joints. The rotating elements may be rotational joints. Alternatively, various 3D shapes/structures (e.g., pyramidal) may be formed by having different combinations of the design parameters. Alternatively, each of the flexible linkage portions 111 to 115, 141 to 145 may be a plurality of linkage portions.

Figure 4A:
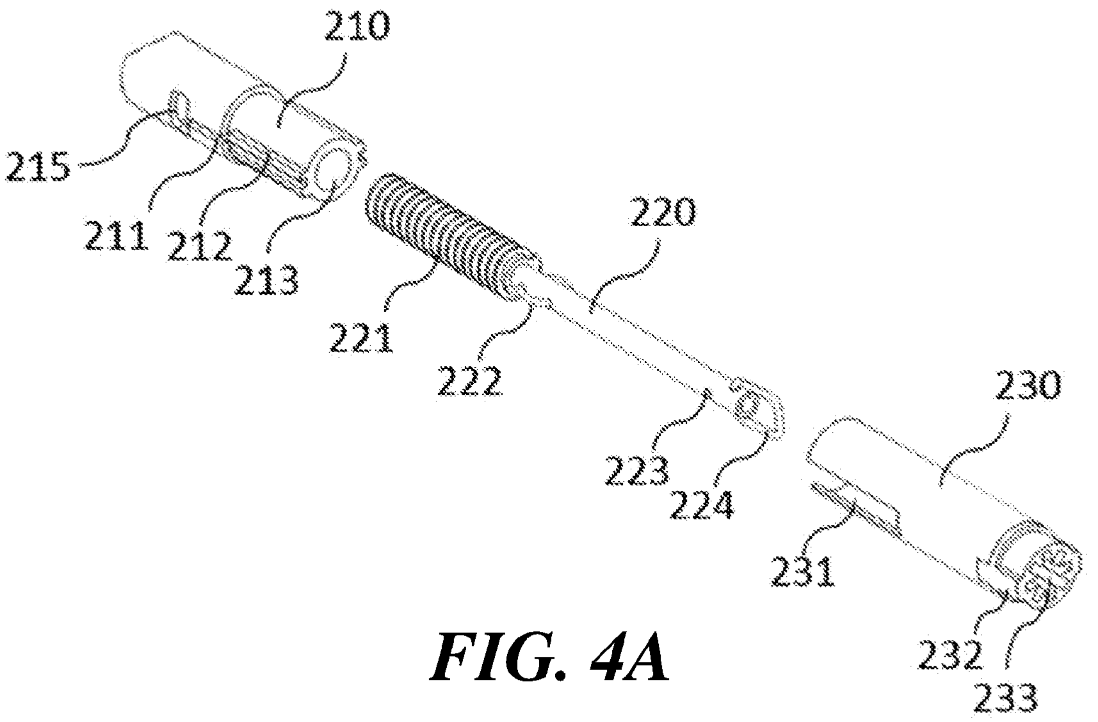
FIGS. 4A and 4B are exploded cross-sectional views of an actuation and lock mechanism of the lumen expansion device in accordance with the present embodiments.
Figure 4B:
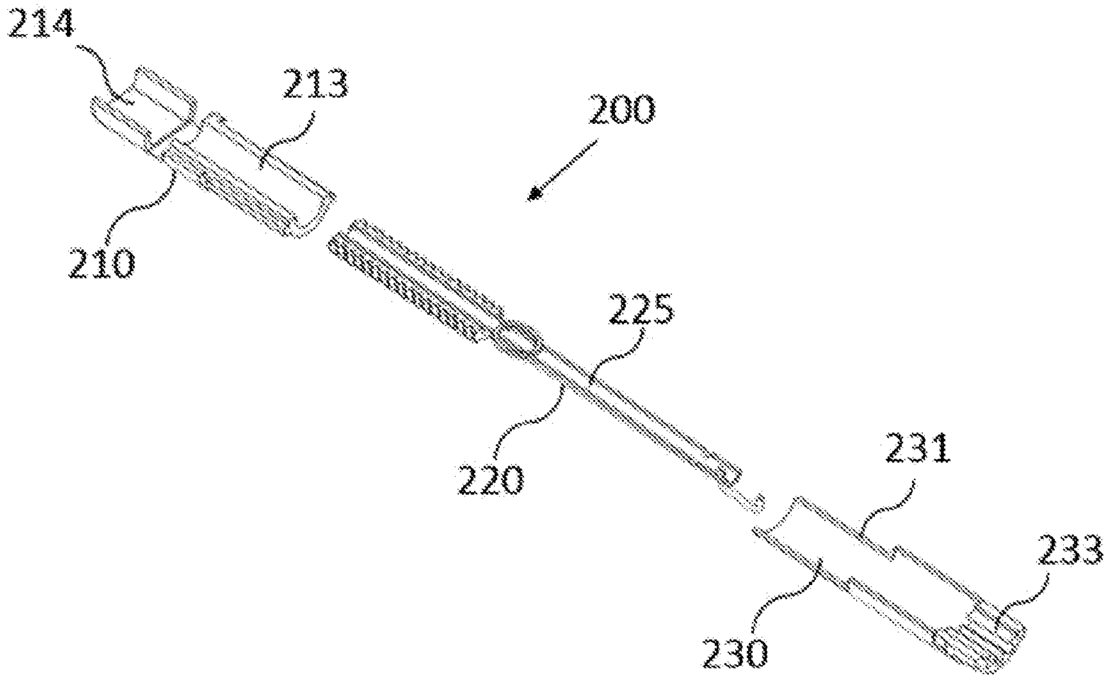

Referring to FIGS. 4A and 4B, the actuation and lock mechanism 200 is depicted and, in accordance with the present embodiments, comprises three parts: an actuation base 210, an actuation rod 220, and a locking cap 230. The actuation base 210 includes windows 215 located about a distal end of the actuation base 210, and grooves 211 located on the outer surface of the actuation base 210 adjacent to the windows 215, where the actuation line 180 is arranged to go through the windows 215 and the grooves 211. The actuation base 210 further includes ridges 212 located around an outer surface about a proximal end of the actuation base 210, the ridges 212 arranged to act as a guide for the locking cap 230. The actuation base 210 further includes a threaded hole 213 located about a proximal end, and a distal hole 214 located about the opposed end of the threaded hole 213, the threaded hole 213 arranged to accommodate the actuation rod 220, and the distal hole 214 arranged to engage the flexible main structure 100.

The actuation rod 220 includes a threaded portion 221 located around an outer surface about a distal end of the actuation rod 220, the threaded portion 221 arranged to fit into the threaded hole 213. The actuation rod 220 further includes a protruding lock key 222 located adjacent to the threaded portion 221. On the inner surface of the actuation rod 202 is a hollow tube 225, the hollow tube 225 arranged to provide a passageway for the tissue block wire 181. An L-hook hole 223 and the U-hook loop 224 are located about a proximal end of the actuation rod 220 arranged to join with the manipulation rod 400.

The locking cap 230 includes slots 231 located about its distal end, the slots 231 arranged to be slid into the ridges 212 of the actuation base 210. A male connector 232 is located on the outer surface about a proximal end of the locking cap 230, the male connector 232 being arranged to engage a corresponding female connector 330 on the manipulation tube 300. The locking cap 230 further includes key slots located about its proximal end, the key slots 233 having a plurality of slots, each slot arranged to engage the lock key 222 such that the actuation and locking mechanism 200 is in a locking position.

Figure 5:
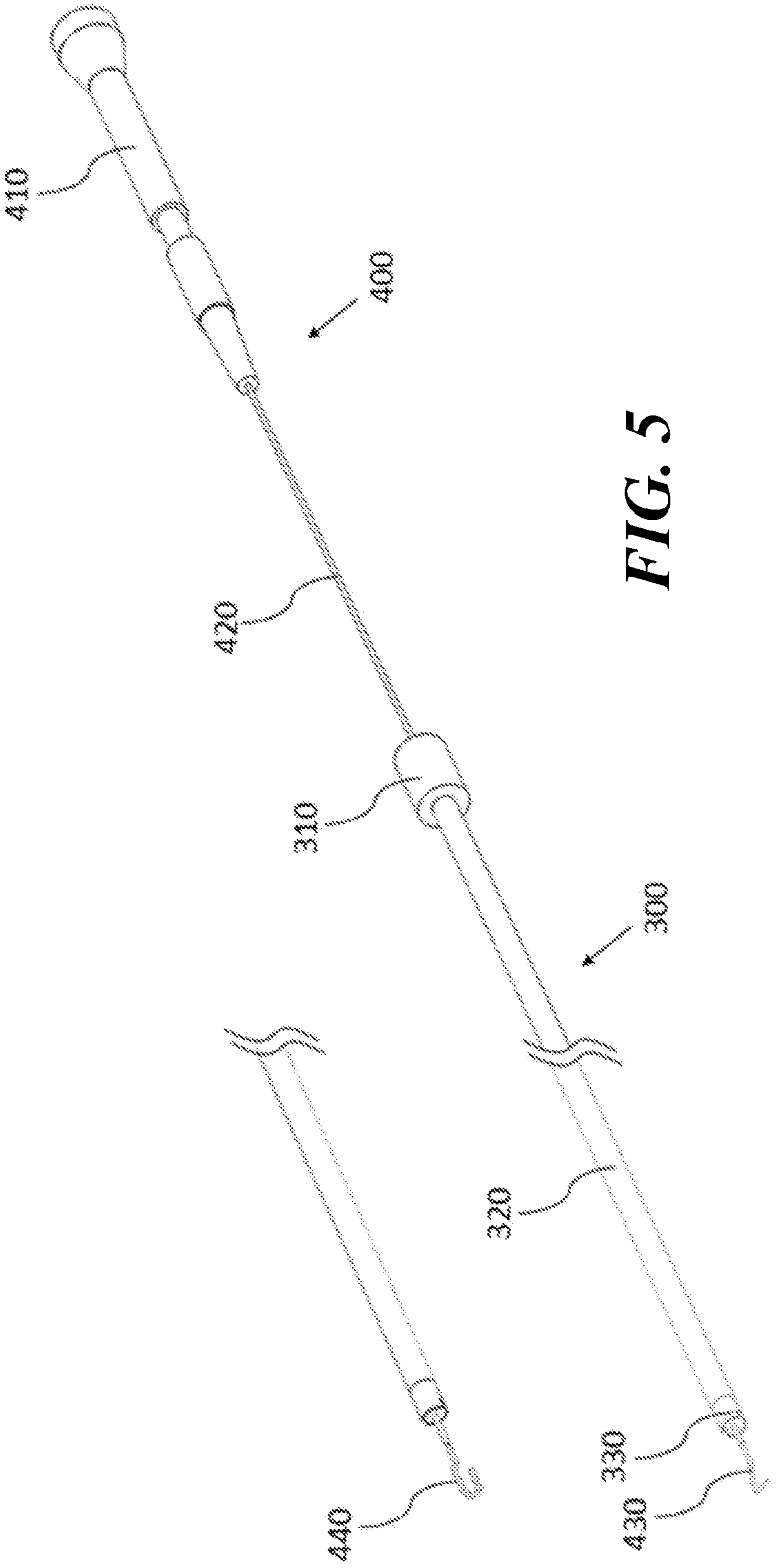
FIG. 5 is a perspective view of a manipulation rod and manipulation tube of the lumen expansion device in accordance with the present embodiments.

Manipulation of the actuation and lock mechanism 200 in accordance with the present embodiments enables deployment of the left and right flexible tube linkages 100, 140 to form the 3D structure creating the interluminal volume at the workspace for visualization and tool/instrument manipulation. In accordance with the present embodiments, the actuation and lock mechanism 200 can be manipulated by a user at the proximal end of the flexible assembly (e.g., the endoscope) by manipulation of the manipulation tube 300 and the manipulation rod 400 as described hereafter in regard to FIG. 5. A cylindrical handle 310 is positioned on a proximal end of the manipulation tube 300, the handle 310 being arranged for manipulation of the manipulation tube 300, where manipulation includes the motions of actuating, twisting, and rotating. The manipulation tube 300 includes a flexible manipulation tube 320 extending from the handle 310; a female connector 330 is located on a distal end of the flexible manipulation tube 320 extending from the flexible manipulation tube 320, the female connector 330 being dimensioned to fit the male connector 232 (FIG. 4A) of the actuation and lock mechanism 200. The manipulation tube 300 is coupled to a manipulation rod 400, where the manipulation rod 400 includes a rod handle 410 located on its proximal end for manipulation of the device. A long flexible rod 420 extends from the rod handle 410 and exits through the manipulation tube 300. An L-hook 430 is located on the exited end of the long flexible rod 420 where the L-hook 430 is protruding out of the manipulation tube 300. Alternatively, a U-hook 440 may be located on the flexible rod 420 and protruding out of the manipulation tube 300. Alternatively, other shaped hooks (e.g., other letter-shaped hooks) may be located on the flexible rod 420. Alternatively, the handle 310 may be circular shaped instead of cylindrical shaped, or may be shaped in any three-dimensional shape to accommodate a user's hand.

Figures 6A, 6B, 6C:
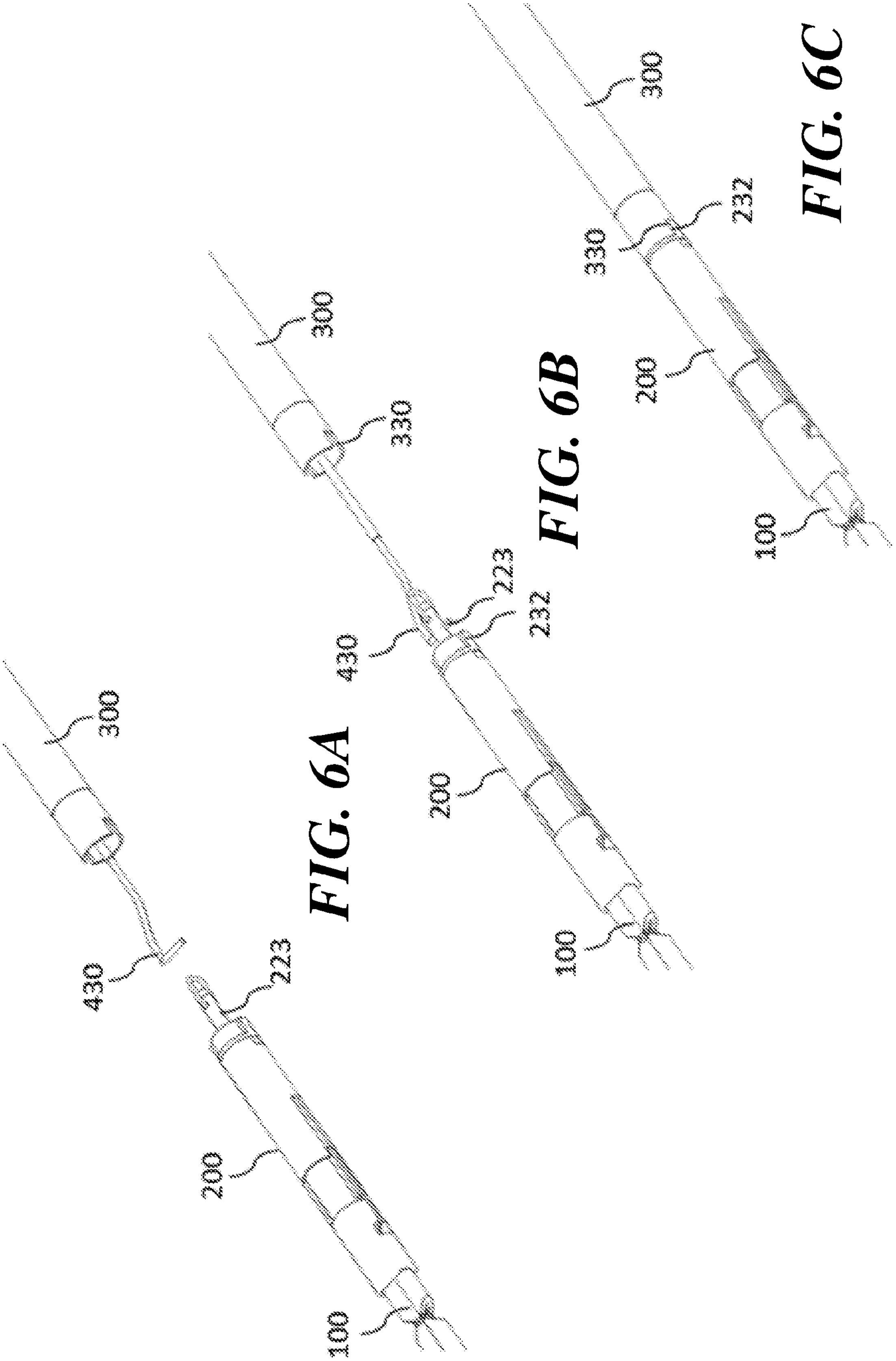
FIGS. 6A to 6C depict a process of connecting a manipulation rod and manipulation tube to the lumen expansion device before delivery in accordance with the present embodiments.

FIG. 6A to 6C illustrate a process of joining the manipulation rod 400 and manipulation tube 300 to the proximal end of the actuation and lock mechanism 200 in preparation for the delivery of the device in accordance with the present embodiments. Referring to FIG. 6A, the manipulation tube 300 with the exposed L-hook 430 is bought into proximity to the proximal end of the actuation and lock mechanism 200 and the L-hook hole 223. Referring to FIG. 6B, the L-hook 430 is arranged to fit into the L-hook hole 223 and the manipulation tube 300 is arranged to slide into contact with the proximal end of the actuation and lock mechanism 200 such that the female connector 330 engages with the corresponding male connector 232, placing the manipulation tube 300 and the actuation and lock mechanism 200 in an engagement configuration. FIG. 6C shows the manipulation tube 300 and the actuation and lock mechanism 200 in the engagement configuration where the device is ready to be delivered through an endoscopic channel. When a rotation motion is applied to the manipulation tube 300 as a result of rotating the handle 410, the engaged L-hook hole 223 rotates relative to the manipulation tube 300, thereby causing the actuation and locking mechanism 200 to rotate for deployment of the left flexible tube linkage 110, the right flexible tube linkage 140, the side tube frames 170 and 171, and the distal tube 172 and formation of the 3D deployed structure to provide the workspace volume in accordance with the present embodiments.

Figure 7A:
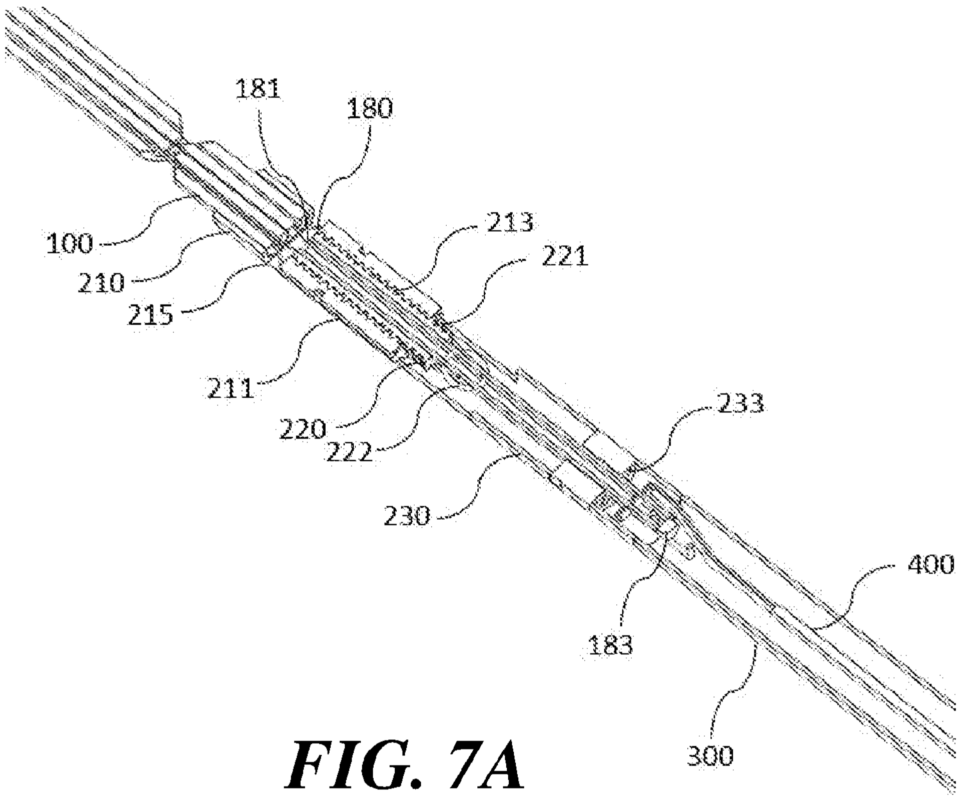
FIG. 7A is a cross-sectional view of an actuation and lock mechanism of the lumen expansion device in accordance with the present embodiments and FIG. 7B is an external view of the lumen expansion device before deployment in accordance with the present embodiments.
Figure 7B:
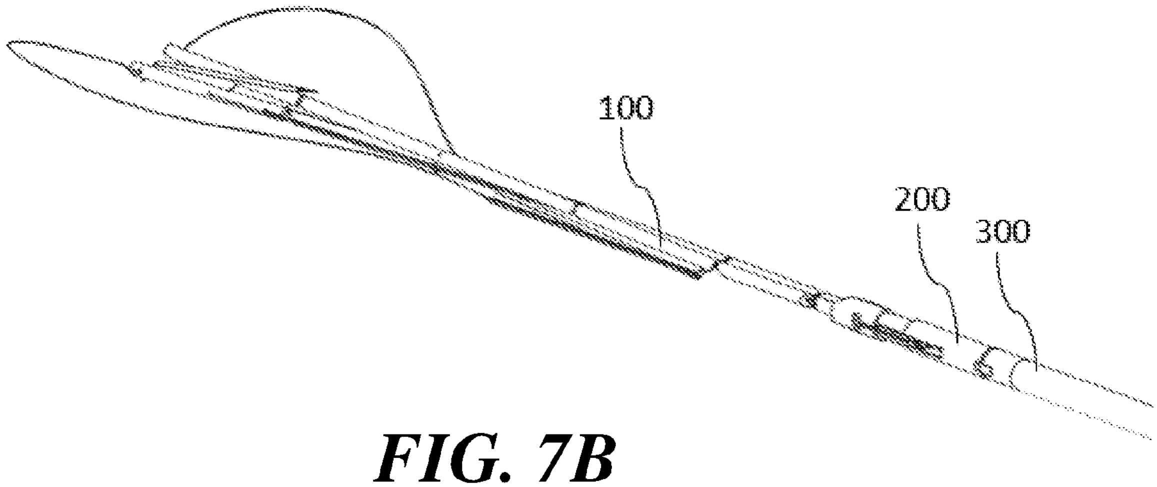

A cross-sectional view of the ready-to-deliver device in accordance with the present embodiments is shown in FIG. 7A. The flexible main structure 100 is fitted into the distal end of the actuation base 210 and may be joined by an adhesive. The actuation line 180 extends out of the flexible main structure 100 and routes outside of the actuation base 210 through windows 215 while passing through groove 211 and terminates at the lock key 222. The tissue block line 181 passes internally through the actuation rod 220 and terminates at the proximal end of the actuation rod 220 with a crimping bead 183. Some slackness may be necessary for the actuation line 180 to couple the deployment motion with the tensioning of the tissue block line 181. In this configuration, a substantial portion of the threaded rod 220 is inside the threaded hole 213 and the lock key 222 is far away from the key slot 233, thus ensuring that there is sufficient distance for pulling the actuation line 180 and the tissue lock line 181. The external view of this configuration is shown in FIG. 7B. Alternatively, the flexible main structure 100 and the actuation base 210 may be joined by corresponding joints or dovetail joints, or by box joints.

Figure 8A:
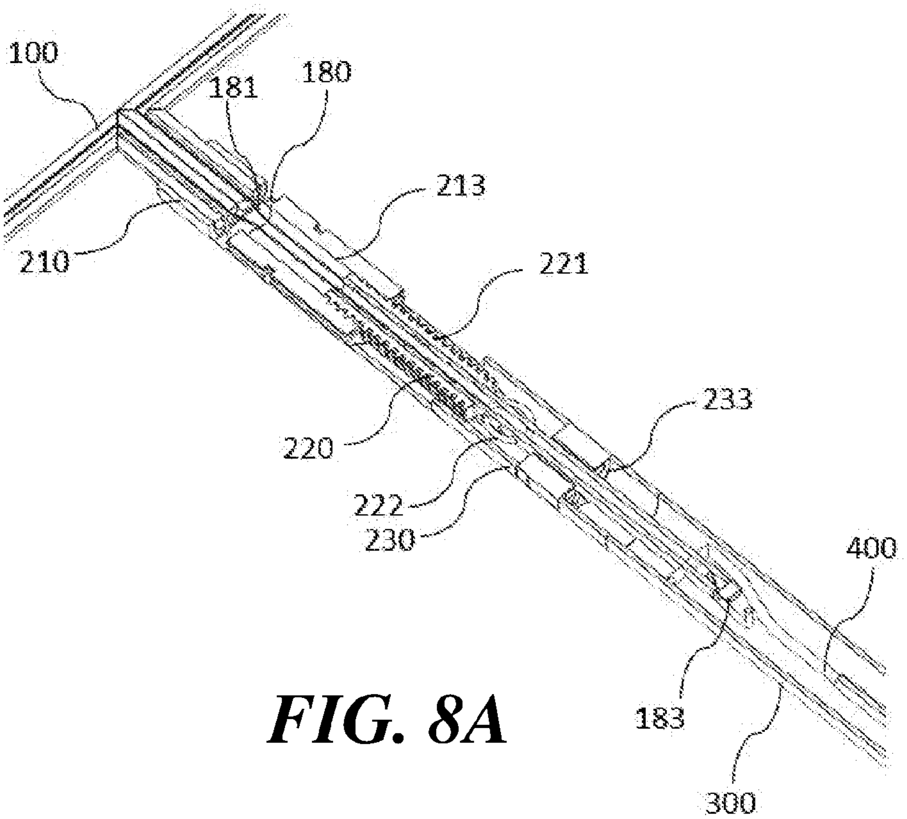
FIG. 8A is a cross-sectional view of the actuation and lock mechanism of FIG. 7A in accordance with the present embodiments and FIG. 8B is an external view of the lumen expansion device when fully deployed in accordance with the present embodiments.
Figure 8B:
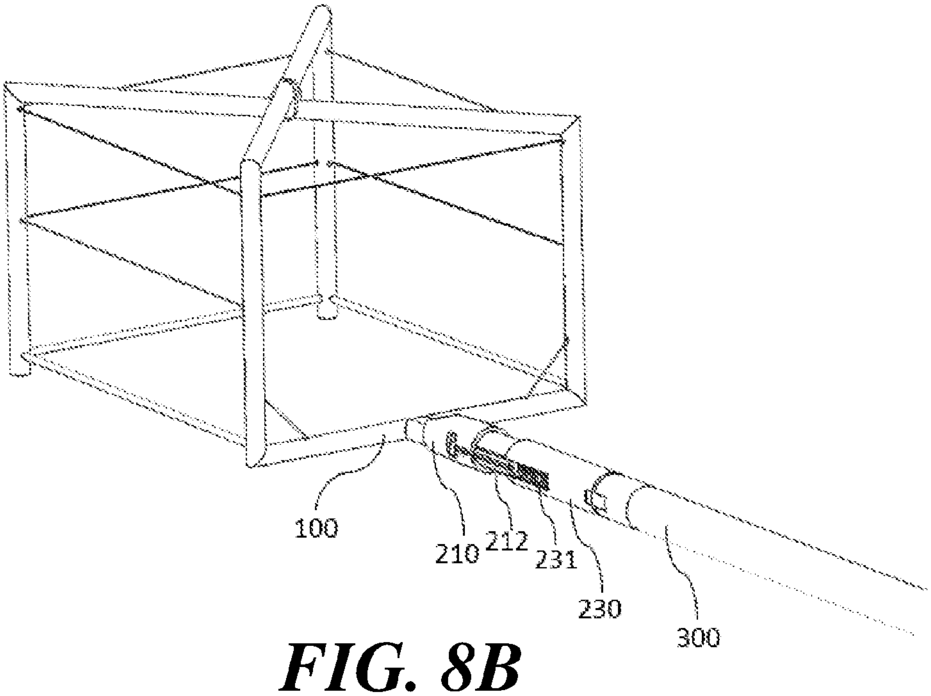

FIG. 8A is a cross-sectional view of the actuation and lock mechanism after the actuation line is pulled in accordance with the present embodiments and FIG. 8B is a cross-sectional view of the device after the actuation line is pulled in accordance with the present embodiments, including the 3D structure forming the volume. The motion of pulling is generated by rotating the manipulation rod 400 and unscrewing the threaded rod 220 out of the threaded hole 213. The manipulation tube 300 is held steady to generate the counter-torque to prevent the device from rotating. The rotational and linear motions of the unscrewing result in winding the actuation line 180 around the threaded rod 221 and pulling the tissue block line 181 due to pushing out the crimping bead 183 by the proximal end at the actuation rod 220. The length of the threaded hole 213 and the threaded portion 221 need to be determined based on the required distance of pulling the actuation line 180 and the tissue block line 181 to transform the device from the closed collapsible shape to the deployed shape (i.e., the length of the threaded hole 213 and the threaded portion 221 is linear to the required pulling distance to transform the device to the deployed shape). When the manipulation rod 400 is pulled towards the manipulation tube 300, the lock key 222 shifts closer to the lock slot 233 leaving a distance therebetween. The external view at this configuration is shown in FIG. 8B, where the flexible main structure 100 forms a tent shape that secures a workspace volume for endoscopic operations. The relative positions of the actuation base 210 and the locking cap 230 are unchanged before and after the actuation (i.e., there is no sliding of the slot 231 along the ridge 212).

Figure 9A:
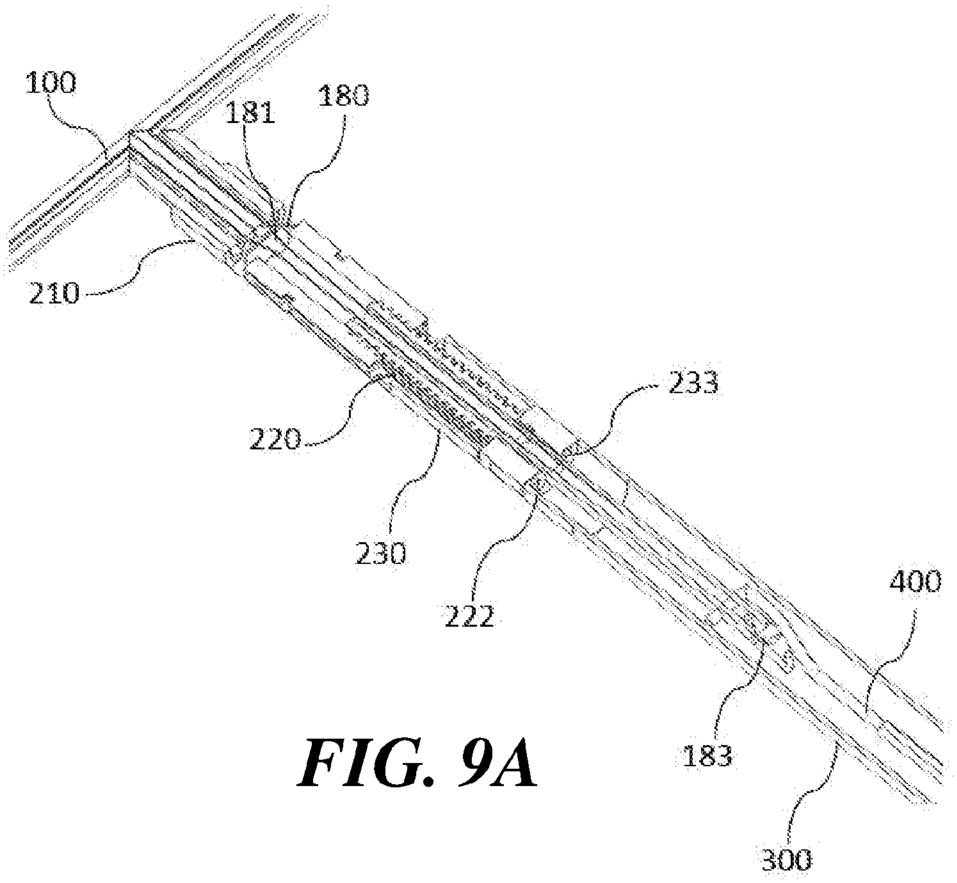
FIG. 9A is a cross-sectional view of an actuation and lock mechanism of the lumen expansion device in accordance with the present embodiments.
Figure 9B:
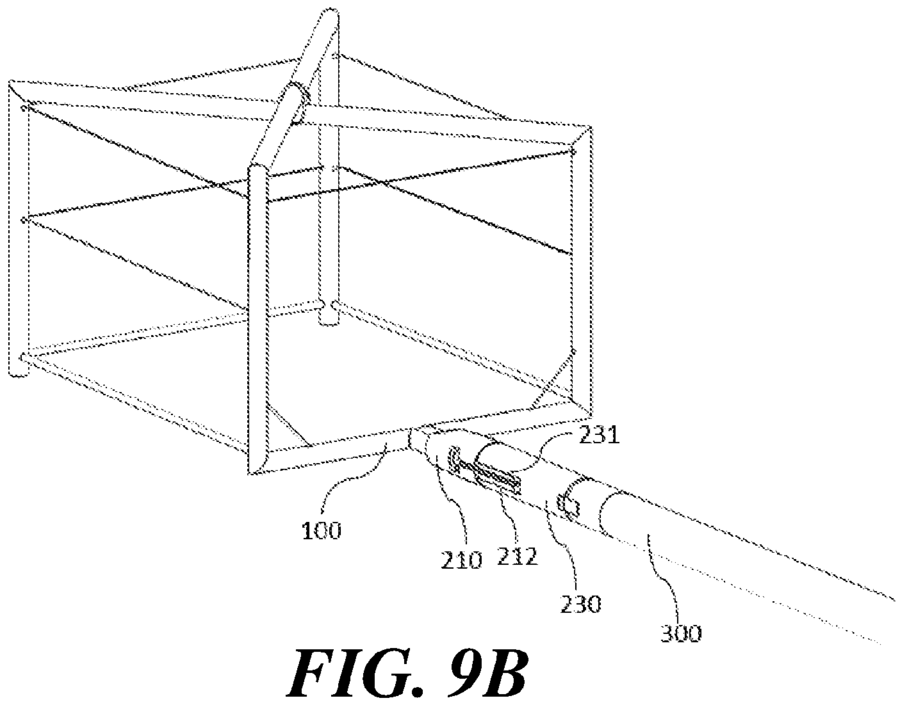
FIG. 9B is an external view of the lumen expansion device when the lumen expansion device is fully deployed and a lock is activated in accordance with the present embodiments.

FIG. 9A is a cross-sectional view of the actuation and lock mechanism 200 and a cross-sectional view of a portion of the device after the lock mechanism is activated in accordance with the present embodiments. The manipulation tube 300 is pushed in from its proximal end to slide in the locking cap 230 until the lock key 222 fits into one of the key slots 233 while the manipulation rod 400 is held steady. Some adjustments to the orientation of the locking cap 230 may be required to align the lock key 222 to one of the key slots 233. Due to the tendency of unscrewing caused by the elasticity of the actuation line 180, friction is generated between the lock key 222 and the lock slots 233, and the locking cap 230 is arranged to prevent the deployed 3D structure from sliding off the actuation base 210. The external view at this state is shown in FIG. 9B, where the locking cap 230 is positioned deeper along the ridges 212.

Figure 10A:
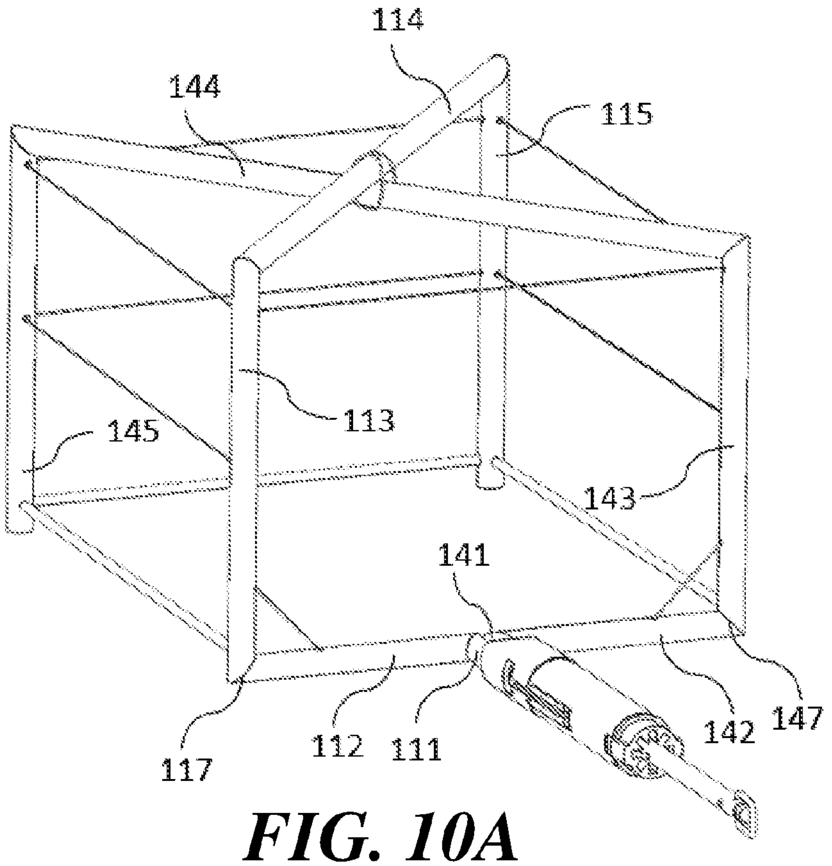
Figure 10B:
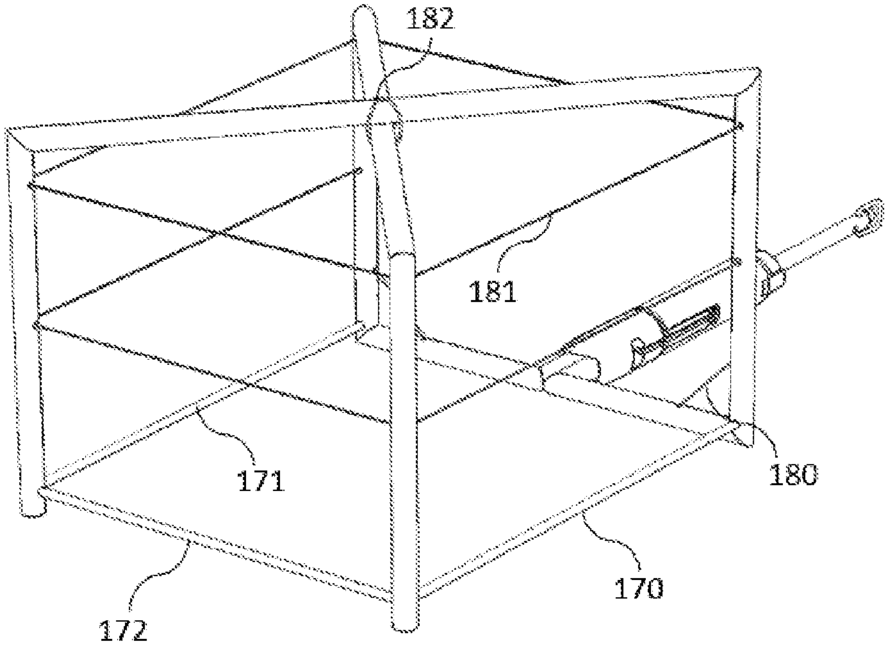

The deployed device in accordance with the present embodiments is illustrated in FIGS. 10A and 10B. The left tube linkage 110 forms portions of the deployed structure encompassing the forward tube 111, the left tube 112, the upper tube 113, the diagonally right tube 114, and the down tube 115, while the right tube linkage 140 is designed to form symmetric portions of the deployed structure including the forward tube 141, the right tube 142, the upper tube 143, the diagonal left tube 144, and the down tube 145. The final deployed structure creates a rectangular box workspace volume for endoscopic procedures, where the rectangular box workspace volume is a hollow space allowing an endoscope and/or medical instruments to pass into. The actuation line 180 goes inside through the face structures (the flexible linkages portions 111, 112, 113, 115, 145, 143, 142, and 141, the side tube frames 170, 171, and the distal tube frame 172). Alternatively, the distal tube frames may be a guiding tube, said guiding tube arranged to provide a passageway for the actuation line 180. The actuation line 180 is exposed outside of the bottom frame at two locations (in between the flexible linkage portions 112 and 113 and the flexible linkage portions 142 and 143). This is to facilitate the actuation motion of their in-between joints 117 and 147. The other joints are naturally rotated to their limits while the actuation line is being pulled. The tissue block line 181 on the side and distal faces are arranged in relation to the plurality of flexible tube linkages 110, 140 to prevent the surrounding tissue from squeezing into the created space or volume in the lumen. The proximal and bottom faces are left open for the access of the endoscope and space for the endoscopic procedures. The manipulation rod and tube may be detached in the reverse order of the joining process shown in FIG. 6.

Figure 11A:
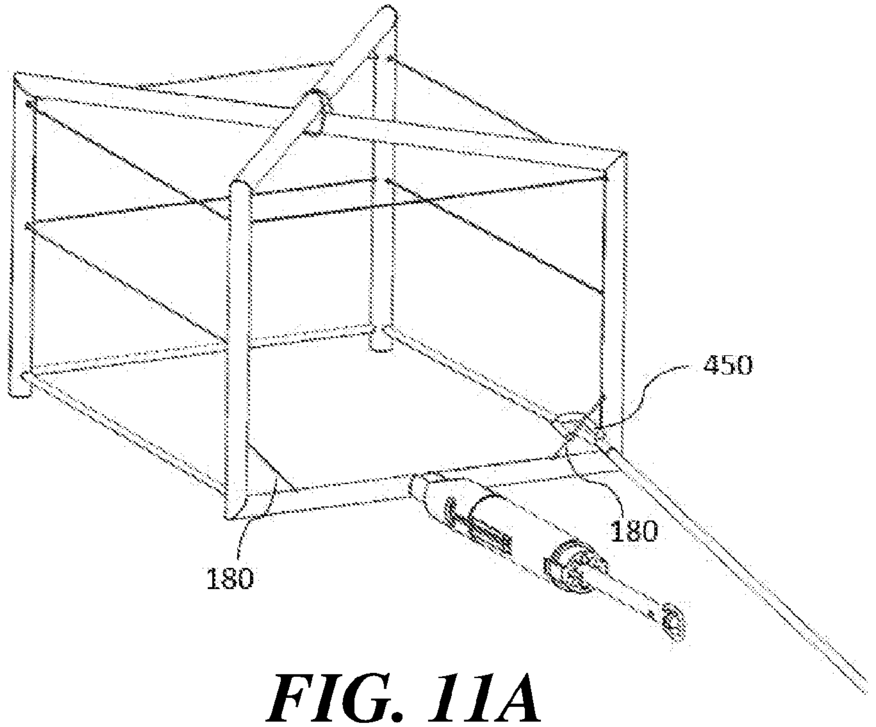
FIGS. 11A and 11B illustrate a process of breaking an actuation line to release tension in accordance with the present embodiments.
Figure 11B:
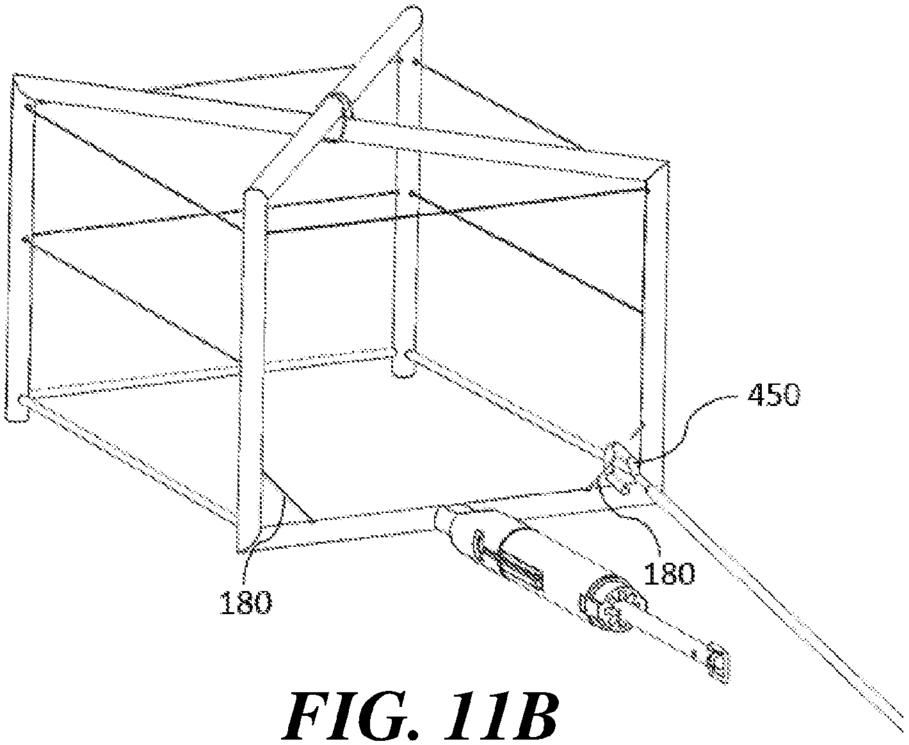

Referring to FIG. 11A, after the endoscopic procedures are completed, the U-hook 440 is introduced to the deployed structure, where the U-hook 440 is arranged to engage one of the exposed actuation lines 180 on the proximal face of the deployed structure to break the actuation line 180 in accordance with the present embodiments. Referring to FIG. 11B, to break the one of the exposed actuation lines 180, the U-hook is rotated on the engaged exposed actuation line thereby releasing tension in the actuation line and collapsing the deployed structure, advantageously providing a simple and easy means to render the collapsed structure flexible for removal from the lumen.

Figure 12A:
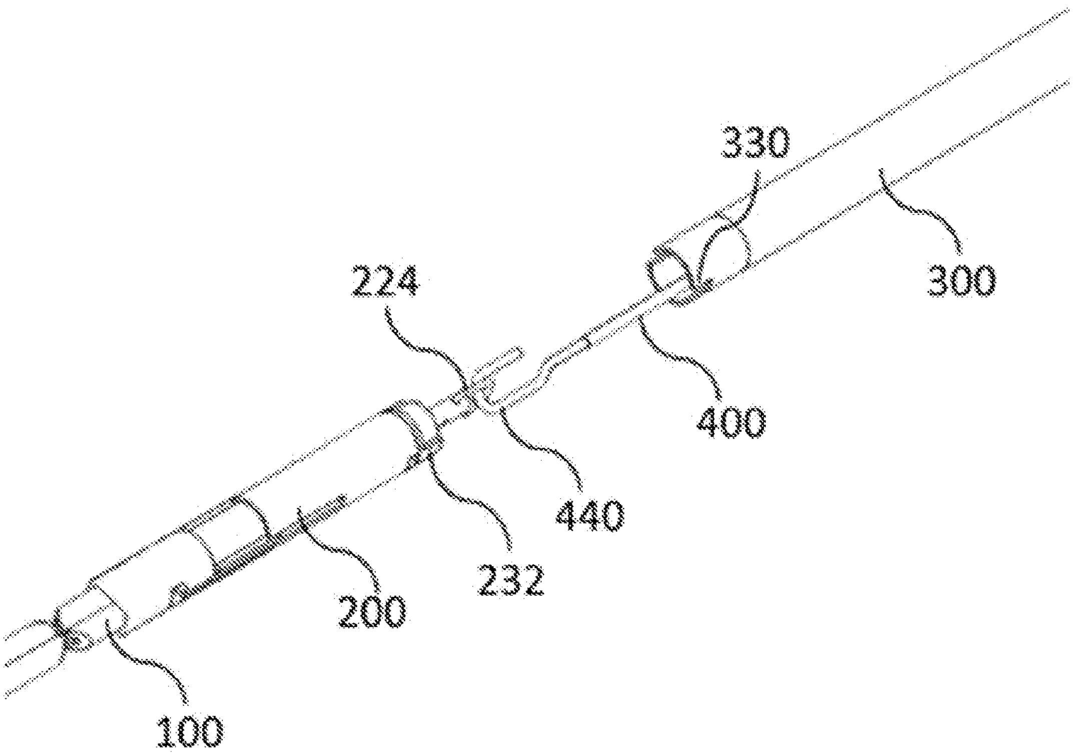
FIGS. 12A and 12B illustrate a process of connecting a device to a manipulation rod and tube for retraction in accordance with the present embodiments.
Figure 12B:
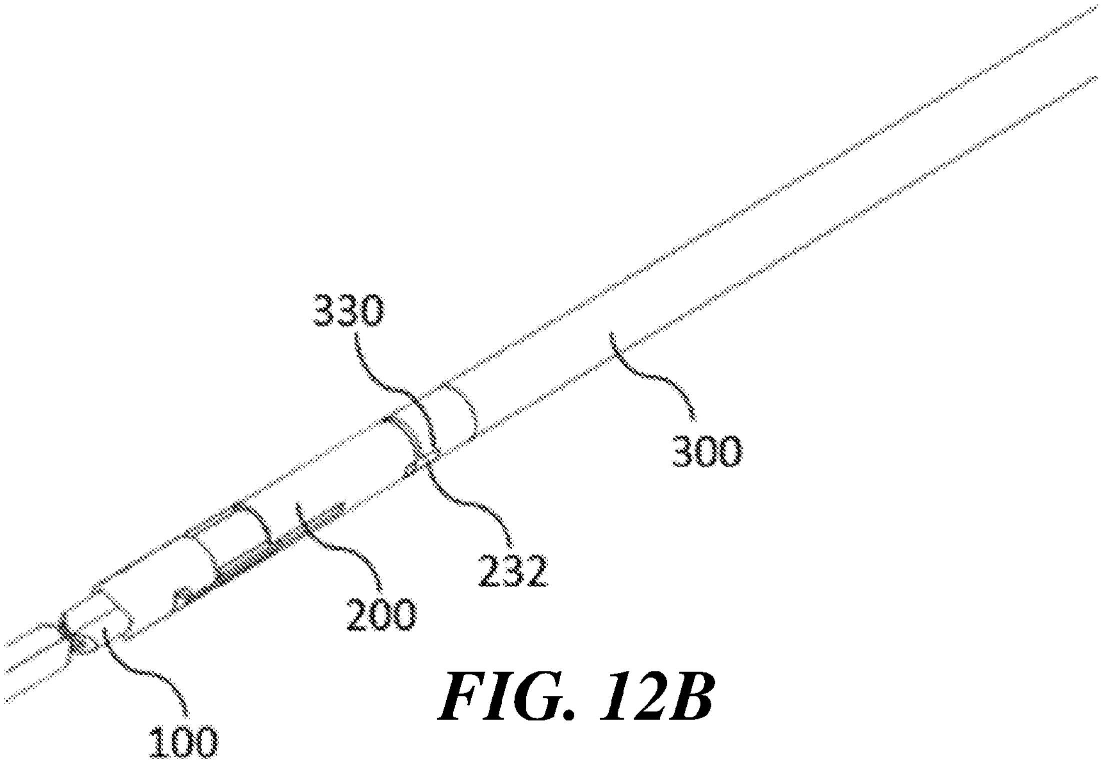

FIGS. 12A and 12B illustrate a process of re-joining the manipulation rod 400 and the manipulation tube 300 to the proximal end of the actuation and lock mechanism 200 in preparation for the retraction of the device in accordance with the present embodiments. The U-hook 440 is hooked through the U-hook loop 224 to couple the U-hook 400 and the U-hook loop 224. Then, the manipulation tube 300 is slid to join the female connector 330 and the male connector 232. The device may then be retracted through an endoscopic channel by applying a linear motion to the manipulation rod 440, thereby pulling the engaged U-hook loop 224 and U-hook 400 and consequently pulling the flexible collapsed structure through the endoscopic channel.

Figure 13:
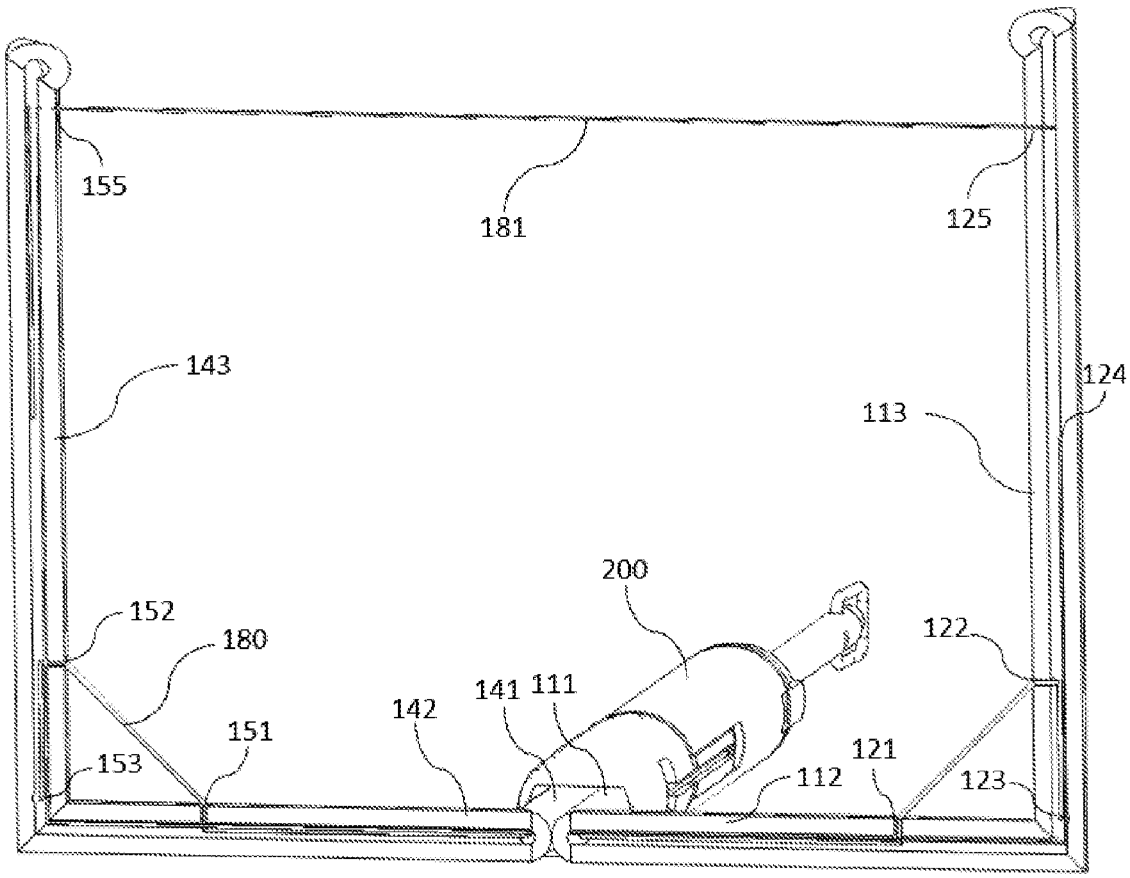
FIG. 13 is a cross-sectional view of a proximal face of the deployed lumen expansion device in accordance with the present embodiments.
Figure 14:
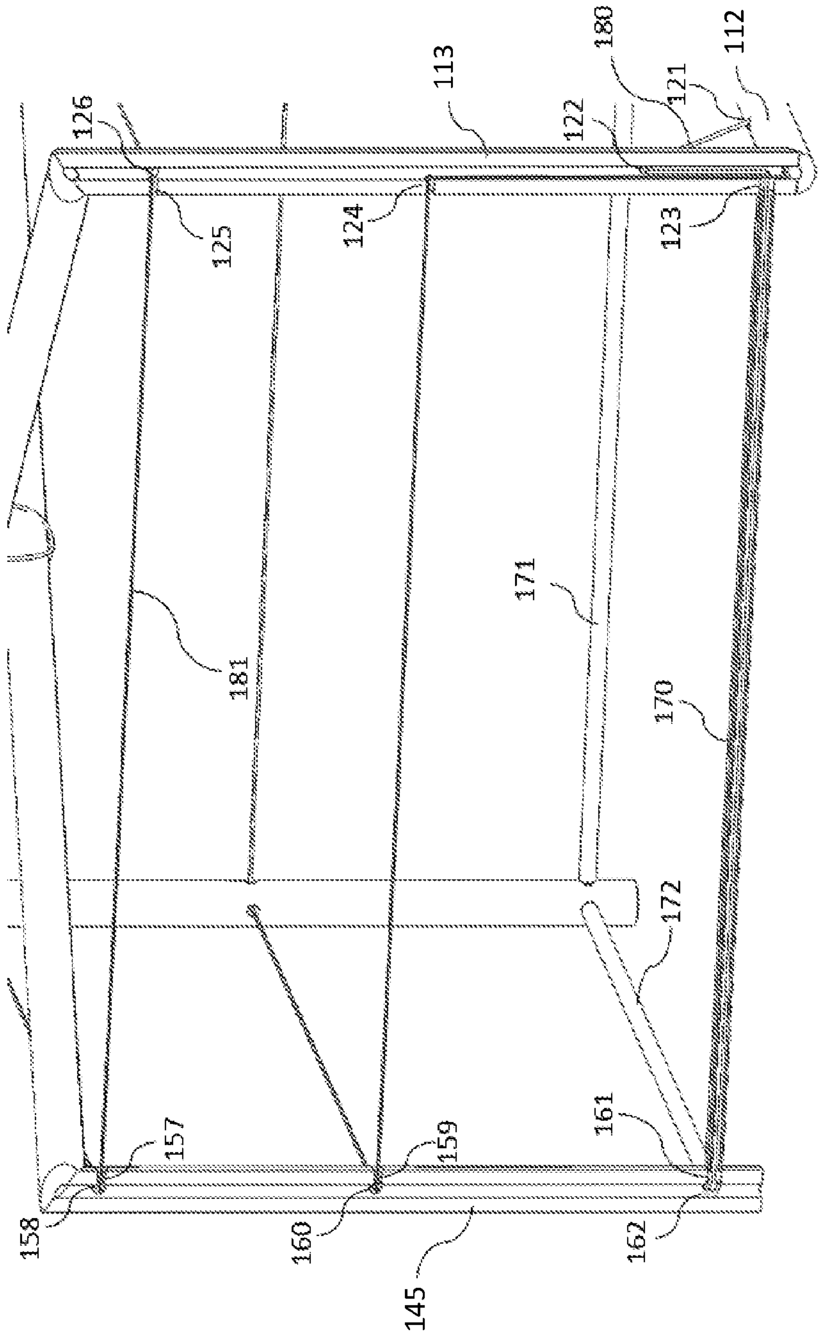
FIG. 14 is a cross-sectional view of a left-side face of the deployed lumen expansion device in accordance with the present embodiments.
Figure 15:
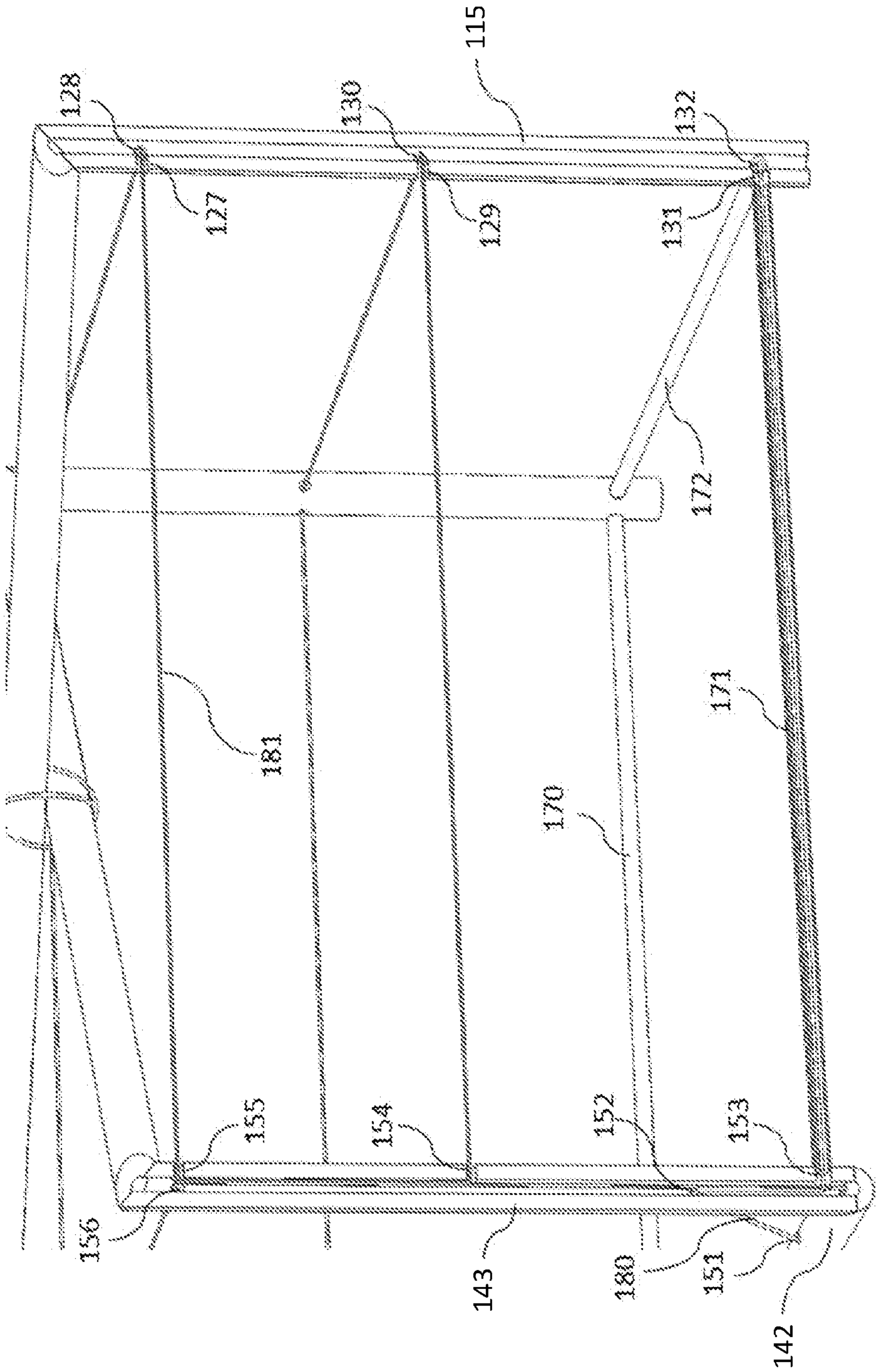
FIG. 15 is a cross-sectional view of a right-side face of the deployed lumen expansion device in accordance with the present embodiments.
Figure 16:
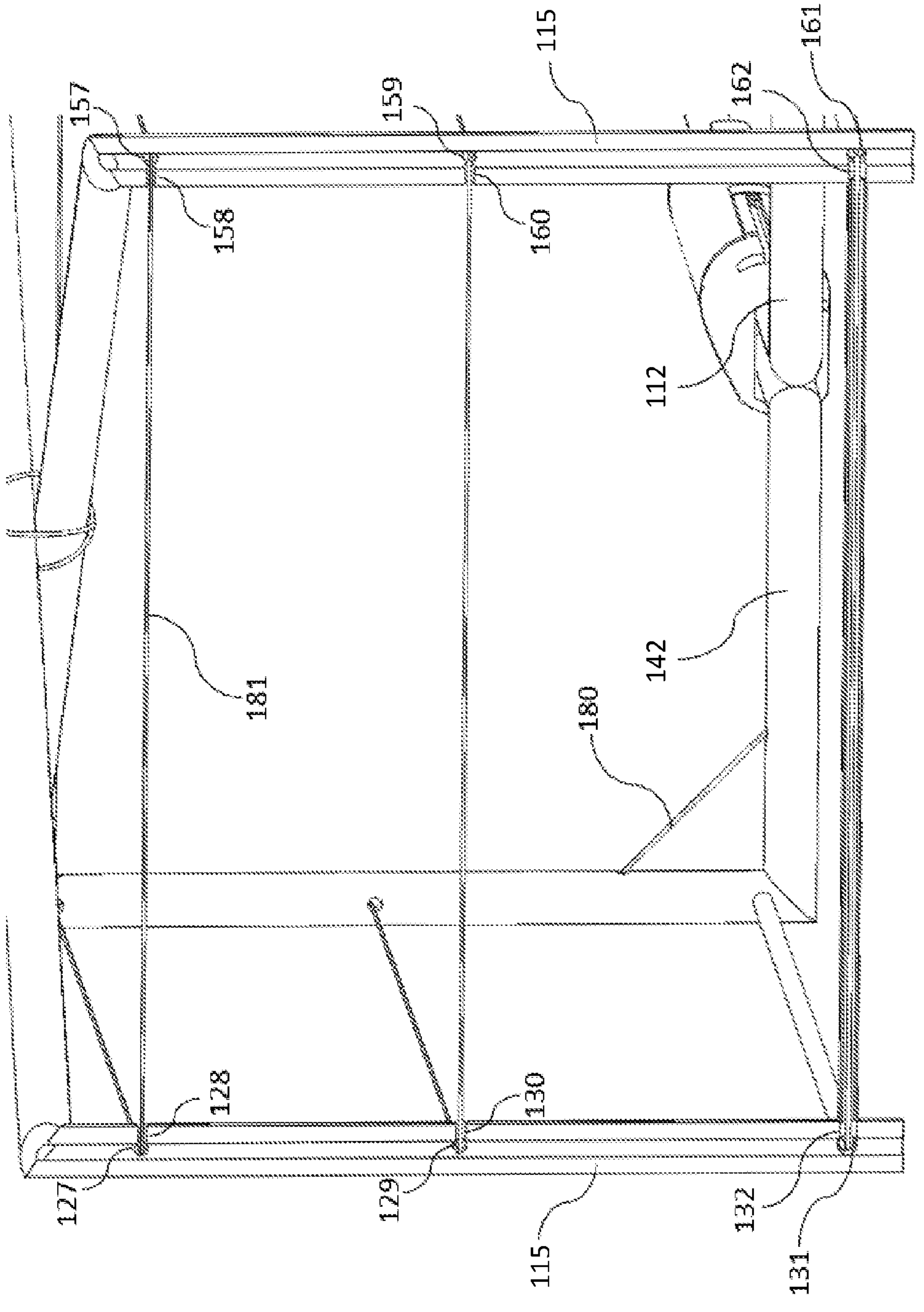
FIG. 16 is a cross-sectional view of a distal face of the deployed lumen expansion device in accordance with the present embodiments.

Referring to FIGS. 13 to 16, cross-sectional perspective views of the deployed lumen expansion device in accordance with the present embodiments are illustrated, wherein FIG. 13 depicts a proximal face view of the deployed expansion device, FIG. 14 depicts a left-side face view of the deployed expansion device, FIG. 15 depicts a right-side face view of the deployed expansion device, and FIG. 16 depicts a distal face view of the deployed expansion device. From the views of FIGS. 13 to 16, it can be seen that the actuation line 180 exits the actuation and lock mechanism 200 and enters the left and right inner tube linkages 111 and 141. From the left and right inner tube linkages 111 and 141, the actuation line 180 goes into second left and right tube linkages 112 and 142 and exits from holes 121 and 151 located on the second left and right tube linkages 112 and 142, respectively. From holes 121 and 151, the actuation line 180 enters third left and right tube linkages 113 and 143 via holes 122 and 152 located about the bottom half of the third left and right tube linkages 113 and 143 and exits by holes 123 and 153 adjacent to holes 122 and 152, respectively. The actuation line 180 then enters inside the side tube frames 170 and 171 located at the bottom of the flexible main structure 100 and travels through side tube frames 170 and 171 and passes through holes 161 and 131 at the opposed end of the side frames 170 and 171 to get inside the fifth tube linkages 145 and 115 perpendicularly coupled to side frames 170 and 171 and exits through holes 162 and 132 located at the bottom of the fifth tube linkages 145 and 115, and from the holes 162 and 132 enters inside the distal tube frame 172 perpendicular the fifth tube linkages 145 and 115 to complete the loop.

As also seen from the views of FIGS. 13 to 16, the tissue block line 181 starts at the actuation and lock mechanism 200, goes through the left tube linkages portions 111, 112, 113, and exits hole 124 located on the left tube linkage portion 113. From the hole 124, the tissue block line 181 runs through the middle of the left side face of the flexible main structure 100, enters hole 159 on the tube linkage 145 and exits from hole 160 adjacent to the hole 159. The tissue block line 181 runs through the middle of the distal face of the flexible main structure 100, enters hole 130 on the tube linkage 115, and exits hole 129 adjacent to the hole 130. The tissue block line 181 intersects in the middle of the right-side face of the flexible main structure 100, enters hole 154 of the tube linkage 143, travels upwards through the tube linkage 143, and exits hole 155 located at the top of the tube linkage 143. The tissue block line 181 then runs across the top of the right-side face of the flexible main structure 100, enters hole 127 at the top of the tube linkage 115 and exits hole 128 adjacent to the hole 127. The tissue block line 181 next runs through the top of the distal face of the flexible main structure 100, enters hole 158, and exits hole 157 of the tube linkage 115. From the hole 157, the tissue block line 181 passes the top of the left side face of the flexible main structure 100, enters hole 125 of the tube linkage 113, exits hole 126 adjacent to the hole 125, intersects the top of the proximal face of the flexible main structure 100, enters the tube linkage 143 via hole 155, and returns to the actuation and lock mechanism 200 through the tube linkages 143, 142 and 141. Alternatively, the actuation line 180 may be arranged to pass inside the joints between tube linkages portions 111 and 112 and between 141 and 142, some holes may be created to pass the actuation line 180 outside of those joints to increase the rotational torque to make the deployment easier. The number and location of the holes 124 to 130 and 154 to 160 on the linkages may be adjusted according to the required location of the tissue block line 181. In addition, some holes may be created on the side and bottom tube frames 170, 171, and 172 to pass the tissue block line through in the case the amount of tissue squeezing needs to be regulated.

Figure 17:
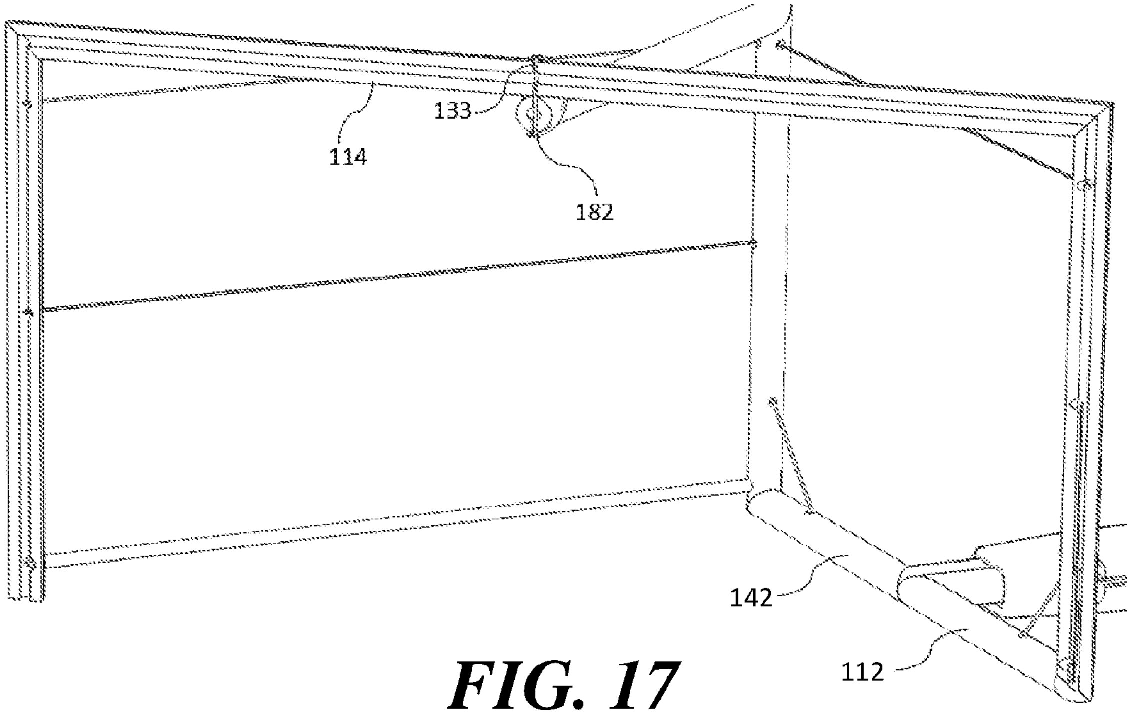
FIG. 17 is a diagonal cross-sectional view of a left linkage of the deployed lumen expansion device in accordance with the present embodiments.
Figure 18:
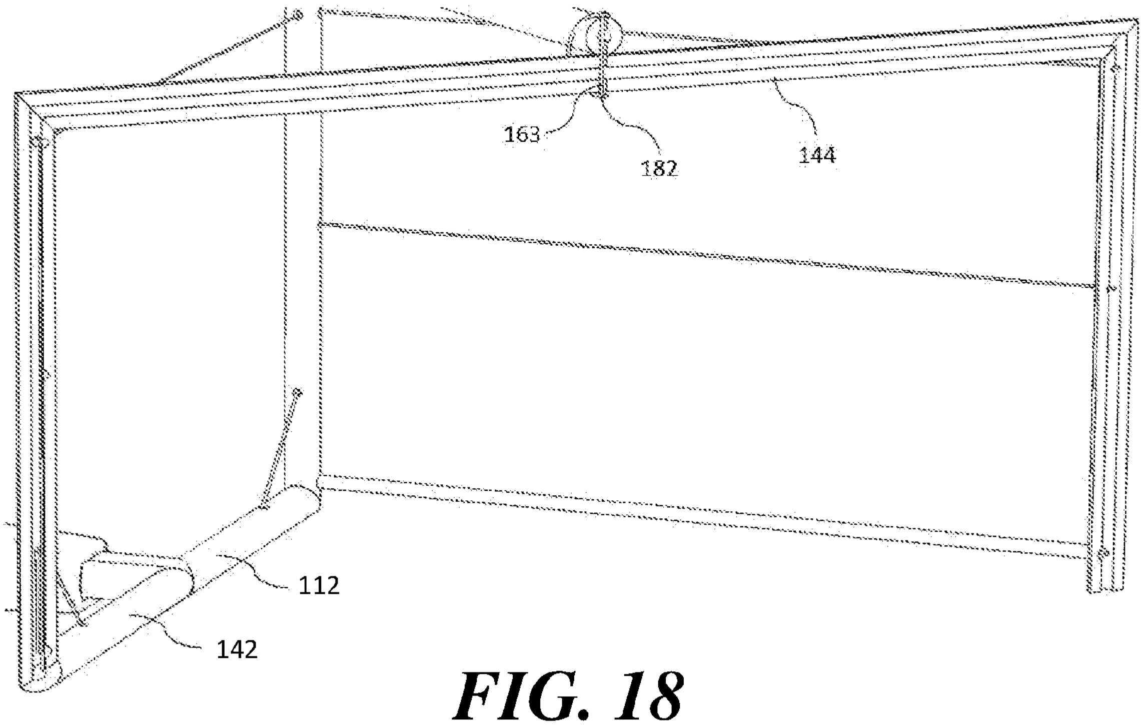
FIG. 18 is a diagonal cross-sectional view of a right linkage of the deployed lumen expansion device in accordance with the present embodiments.

Referring to FIGS. 17 and 18, diagonal cross-sectional views of the left linkage 114 and the right linkage 144 of the deployed lumen expansion device in accordance with the present embodiments are depicted. The flexible elastic line 182 passes through the linkages 114 and 144 located at the top of the structure and goes through hole 133 and hole 163, such that the flexible elastic line 182 wraps outside of the linkages 114, 144 around a point of an intersection, thereby advantageously coupling the left and right tube linkages 110, 140. The elasticity of the flexible elastic line 182 beneficially allows constraining the relative positions of the linkage portions 114, 140 of the left and right tube linkages 110, 140 in accordance with the present embodiments for greater stability and durability of the deployed 3D structure.

Figure 19:
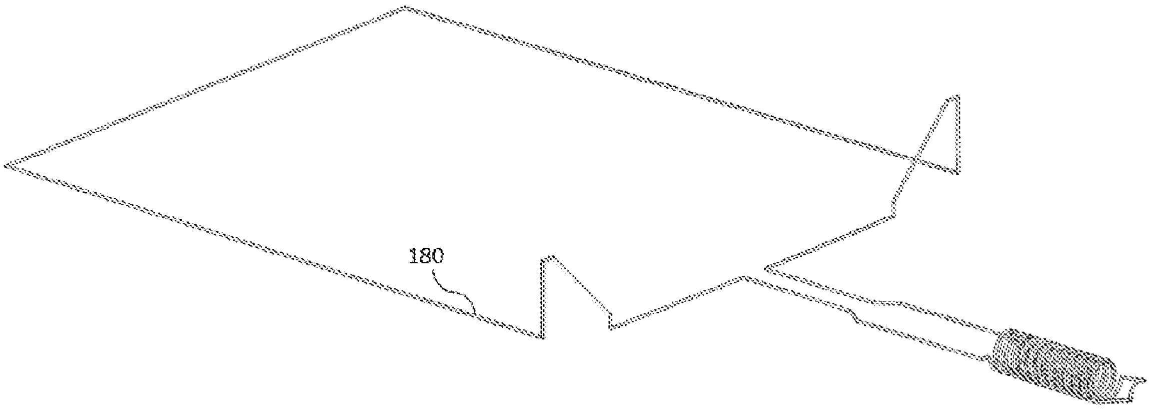
FIG. 19 is a perspective view of the actuation line when the lumen expansion device is deployed in accordance with the present embodiments.
Figure 20:
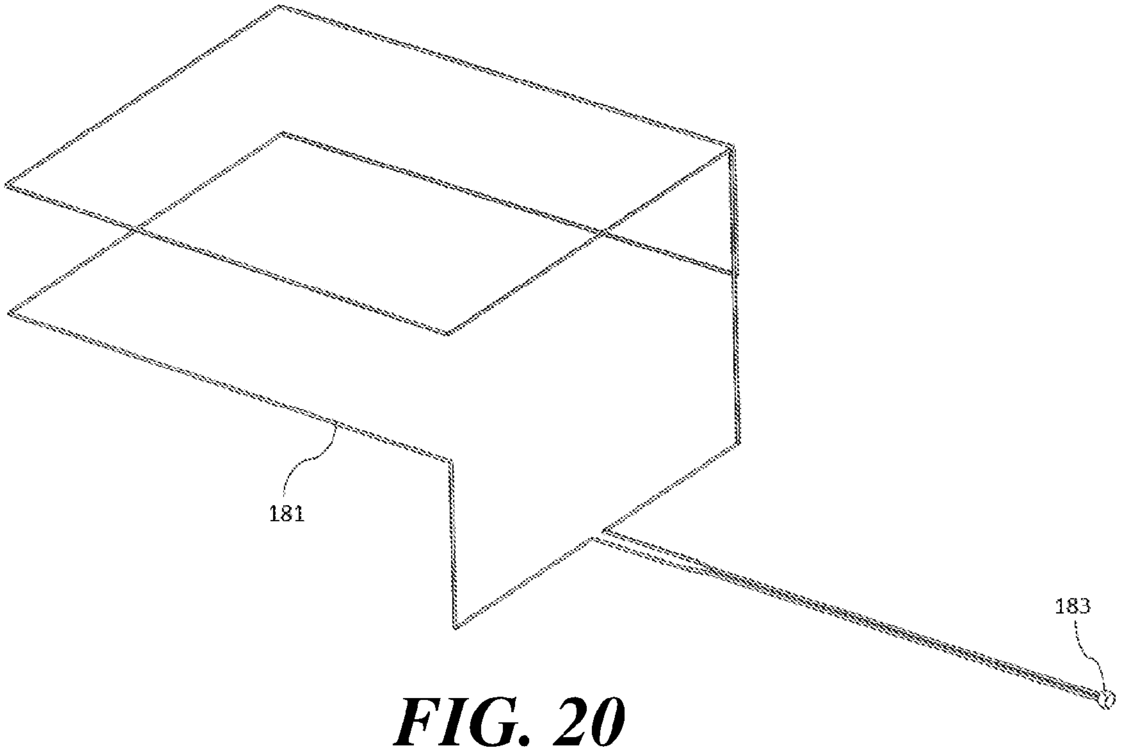
FIG. 20 is a perspective view of a tissue block line when the lumen expansion device is deployed in accordance with the present embodiments.
Figure 21:
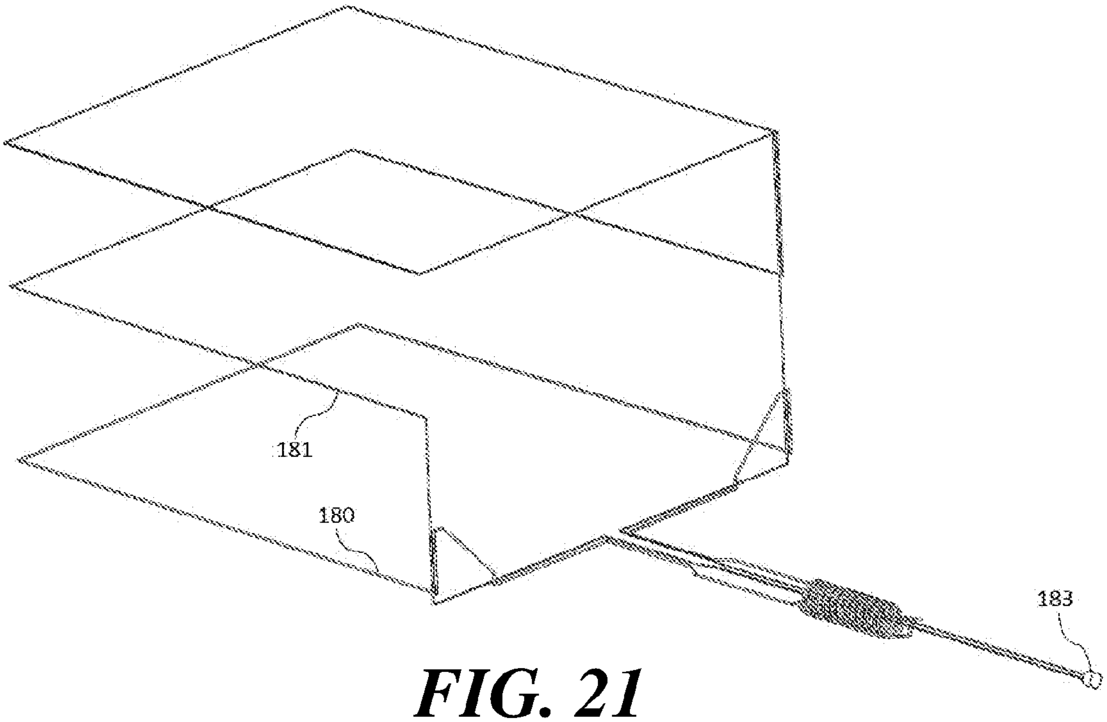
FIG. 21 is a perspective view of both the actuation line of FIG. 19 and the tissue block line of FIG. 20 when the lumen expansion device is deployed in accordance with the present embodiments.

Referring to FIG. 19, when the device is fully deployed, the actuation line 180 forms a shape that forms a base structure for the 3D deployed structure, advantageously pulling the flexible linkages 110, 140 into their deployed positions in accordance with the present embodiments. Referring to FIG. 20, the tissue block line 181 terminates with the crimping bead 183 and, in accordance with the present embodiments, makes a loop to form a top structure and cross open left, right and distal faces for the deployed structure in order to advantageously reduce tissue encroachment into the deployed structure. Referring to FIG. 21, the actuation line 180 and tissue block line 181 are illustrated together in accordance with the present embodiments, showing that they overlay one another.

Figure 22:
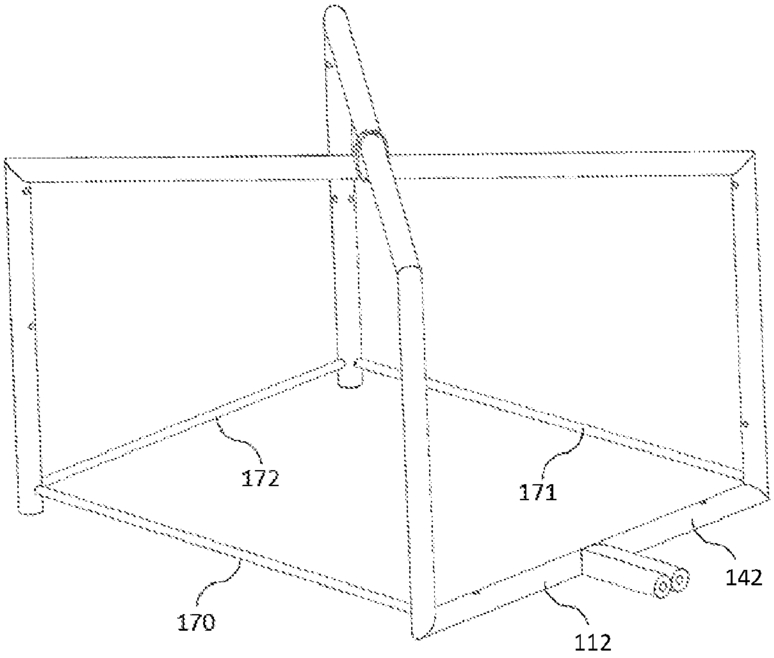
FIG. 22 is a perspective view of a flexible main structure when the lumen expansion device is deployed in accordance with the present embodiments.
Figure 23:
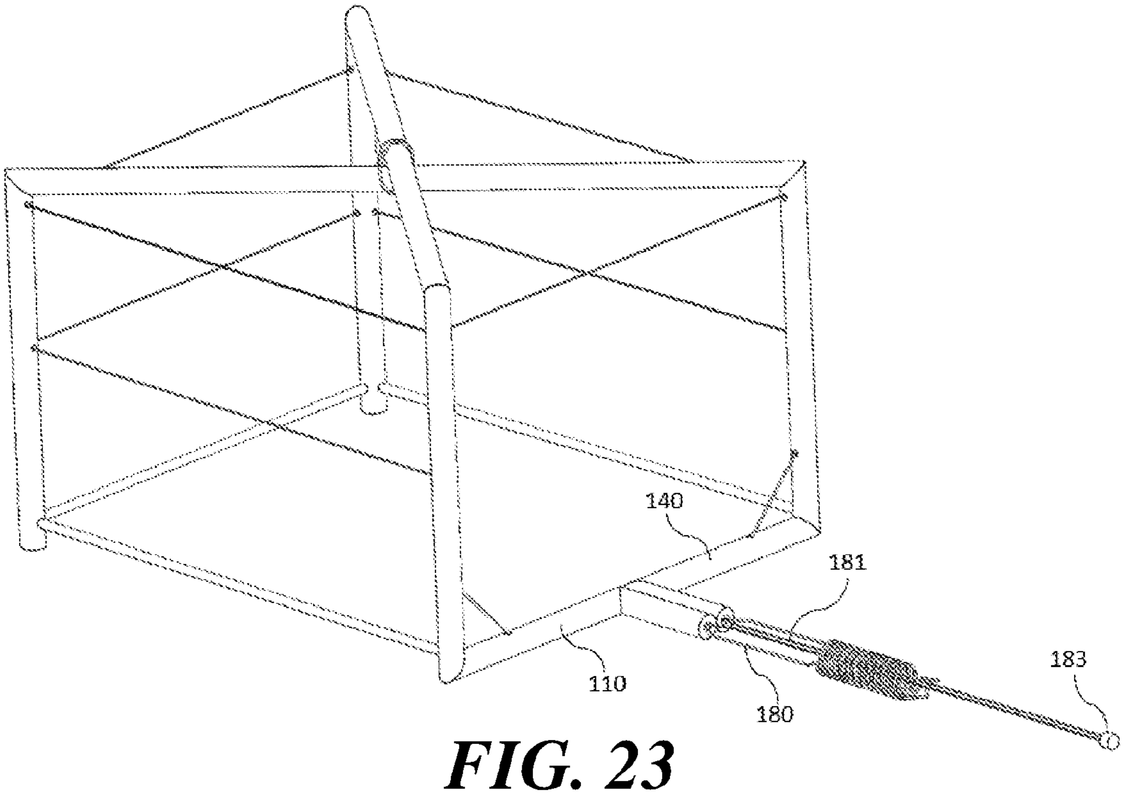
FIG. 23 is a perspective view of a flexible main structure, an actuation line, and a tissue block line when the lumen expansion device is deployed in accordance with the present embodiments.
Figure 24:
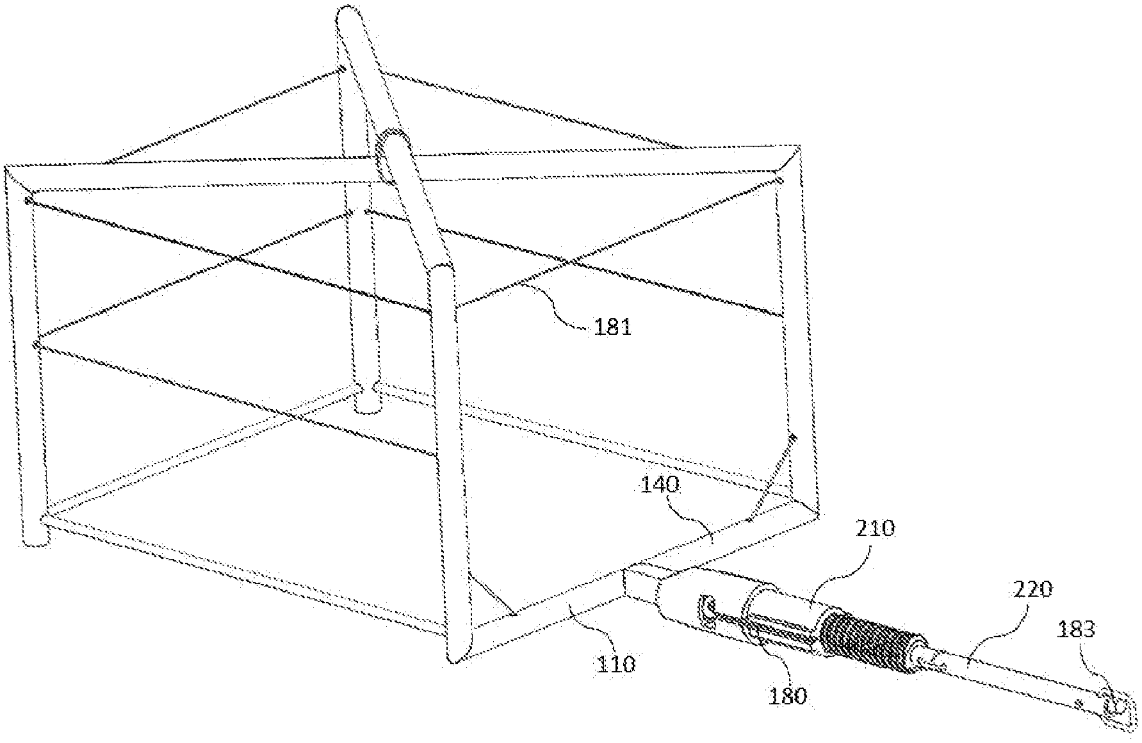
FIG. 24 is a perspective view of a flexible main structure, an actuation base, an actuation rod, an actuation line, and a tissue block line when the lumen expansion device in accordance with the present embodiments is deployed.

FIG. 22 illustrates the flexible main structure 100 (the left and right tube linkages 110, 140 and side tube frame 170, 171, 172) in a deployed 3D configuration in accordance with the present embodiments without the actuation line 180 and the tissue block line 181. FIG. 23 illustrates the deployed 3D configuration of FIG. 22 in accordance with the present embodiments with both the actuation line 80 and the tissue block line 181 where the actuation line has been rotated to pull the flexible main structure 100 into the deployed 3D configuration and the crimping bead 183 has been pulled away from the deployed structure to pull the tissue block line 181 into position. Referring to FIG. 24, the deployed 3D structure, the activation line 180 and the tissue block line 181 illustrated in FIG. 23 are shown together with the actuation base 210 and the actuation rod 220 for deploying the flexible main structure in accordance with the present embodiments.

Figure 25A:
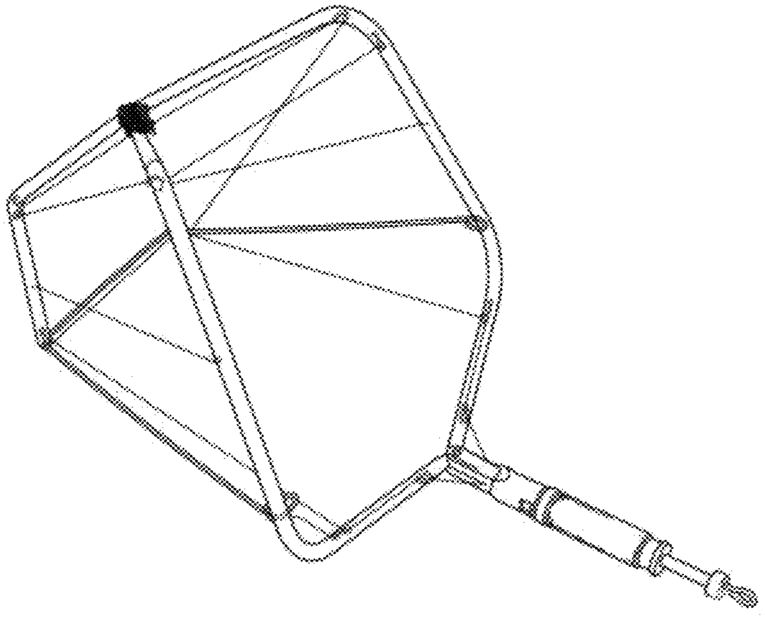
FIGS. 25A and 25B illustrate a deployed structure of the lumen expansion device in accordance with the present embodiments with a small distal face and a large proximal face with rounded joint edges.
Figure 25B:
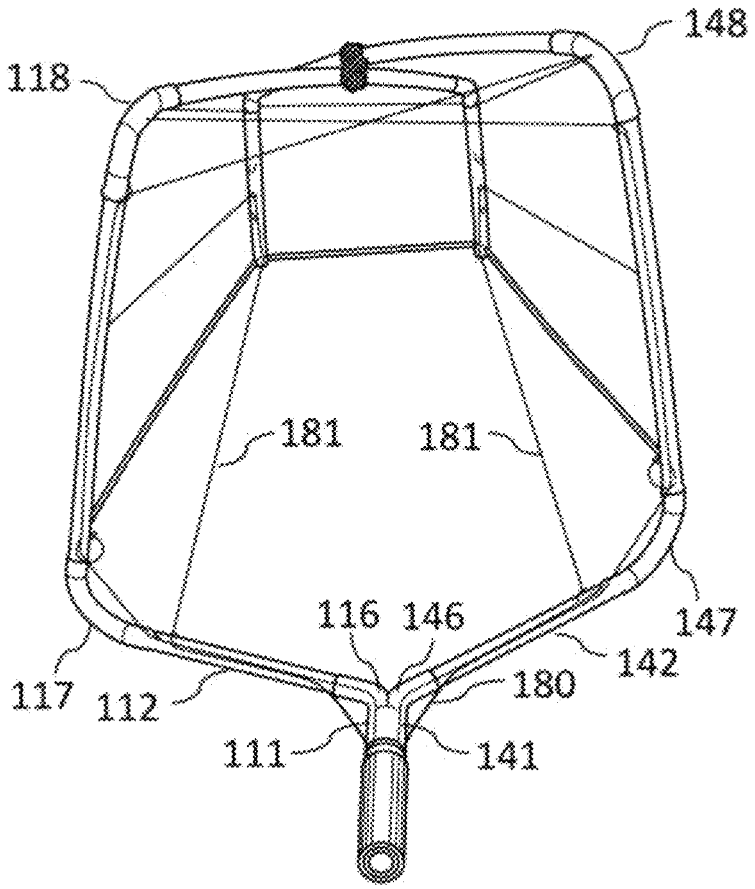

Referring to FIGS. 25A and 25B, a variation of a deployed 3D structure in accordance with the present embodiments is depicted. As can be seen in FIGS. 25A and 25B, the deployed structure has a small distal face and a large proximal face with rounded joint edges. The length of the linkage portions 111 to 115 and 141 to 145 are arranged to form the structure having the small distal face and the large proximal face. The small distal face advantageously reduces the risks of tangling the actuation line and catching tissue by the tip of the structure during deployment. Moreover, with the large proximal face, the deployed structure can be strategically anchored by pressing the surrounding body lumen outward. In addition, the joints on the proximal face 117, 118, 147, 148 can preferably be rounded by creating multiple notches to prevent the risk of damaging tissue adjoining the workspace by sharp edges. Further, the actuation line 180 can be routed outside of the linkages portions 111, 112 and 141, 142 to beneficially increase torque on the rotational joints 116 and 146 to facilitate deployment in accordance with the present embodiments. FIGS. 25A and 25B also illustrate a possible routing for the tissue block wire 181 on a bottom face of the deployed 3D structure.

Figure 26A:
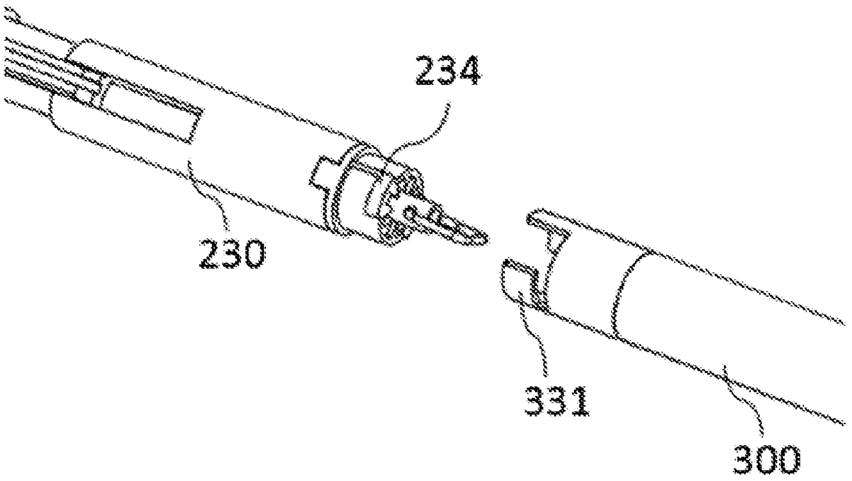
FIGS. 26A to 26C illustrate another embodiment of the connection between a locking cap and a manipulation tube in accordance with the present embodiments.
Figure 26B:
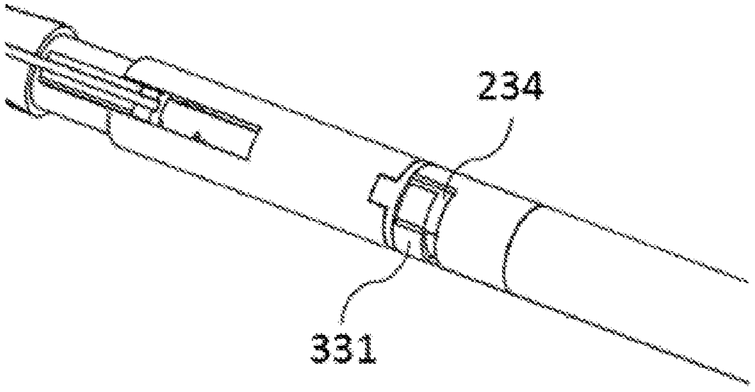
Figure 26C:
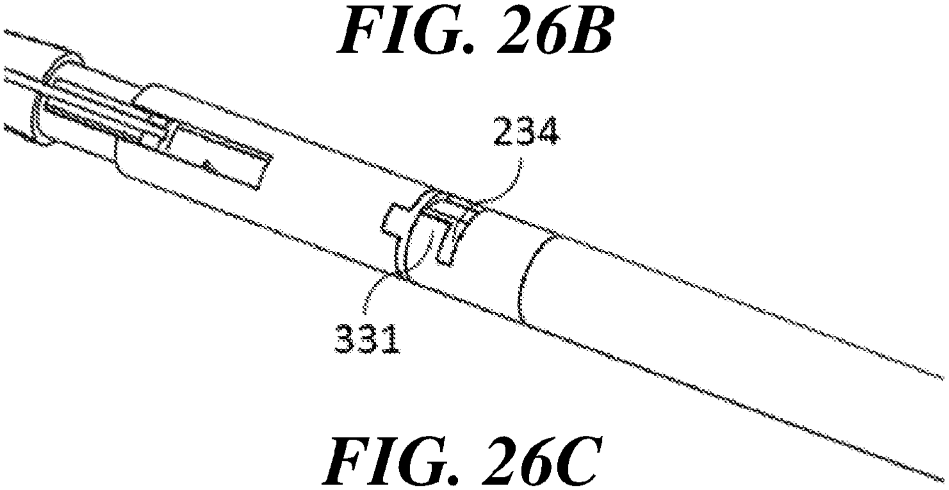

FIGS. 26A to 26C illustrate another embodiment for connecting the locking cap 230 to the manipulation tube 300 in accordance with the present embodiments. After linearly engaging the locking cap 230 with the manipulation tube 300, the manipulation tube 300 may be rotated to fit the L-sockets on the locking cap 230 and on the manipulation tube 331 to prevent accidental disconnection of the manipulation tube 300 from the locking cap 230 during manipulation of the device.

Figure 27A:
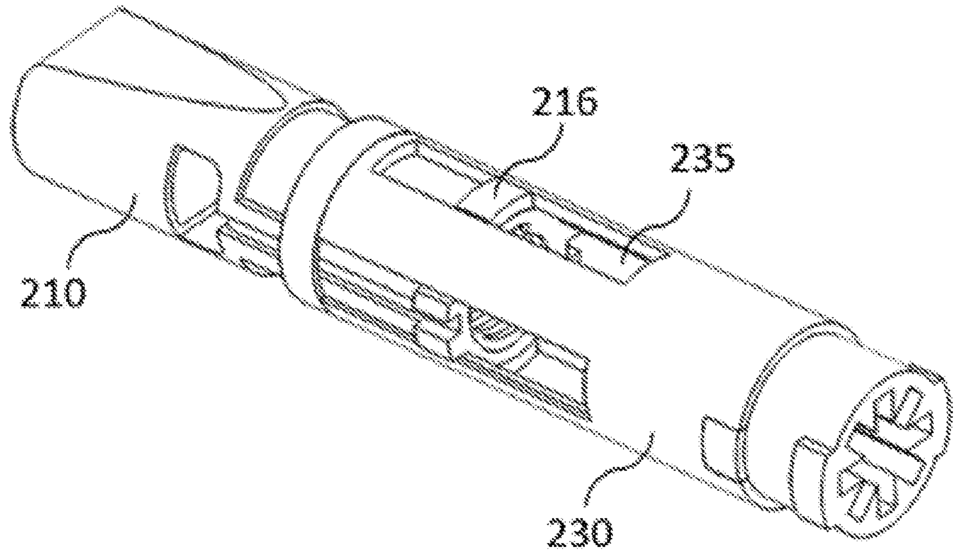
FIGS. 27A and 27B illustrate another embodiment of an actuation base and a locking cap in accordance with the present embodiments wherein the locking cap is engaged with the actuation base.

Referring to FIG. 27A, another embodiment of an actuation base and a locking cap in accordance with the present embodiments is depicted in which the locking cap 230 is engaged with the actuation base 210. In accordance with this embodiment, the actuation base 210 includes a ridge 216 on its proximal end, and the locking cap 230 includes corresponding slots 235. The ridges 216 have raised portions, and each raised portion is dimensioned to fit into a corresponding slot 235. The corresponding slots 235, are enclosed by two horizontal edges and two vertical edges forming a rectangular shape, and each slot has a passageway formed by the vertical edges, allowing the raised portion to slide vertically across the passageway.

Figure 27B:
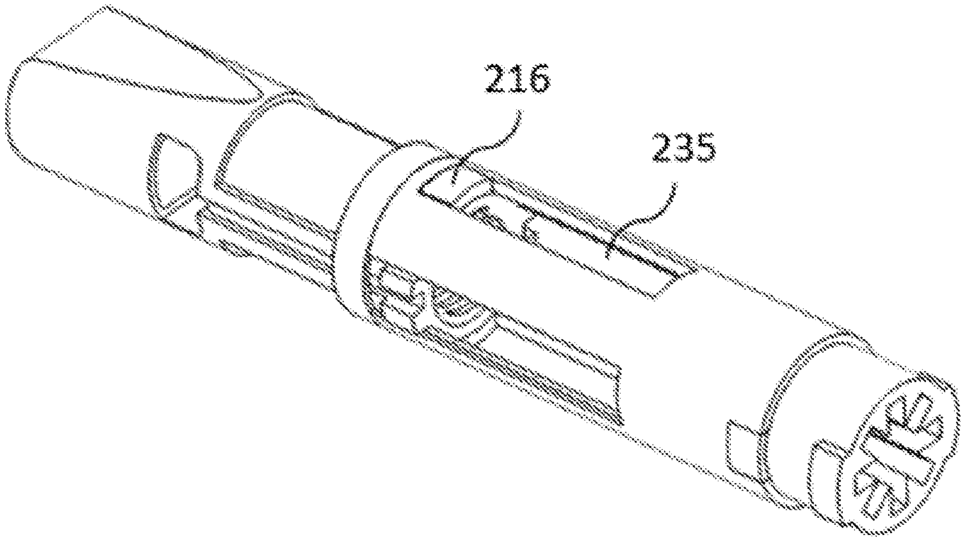

Referring to FIG. 27B, the embodiment of FIG. 27A further depicts the locking cap 230 being moved backward to bring the ridges 216 to meet with one of the horizontal edges of the slots 235, thereby advantageously preventing the locking cap 230 from sliding off the actuation base 210.

Figure 28A:
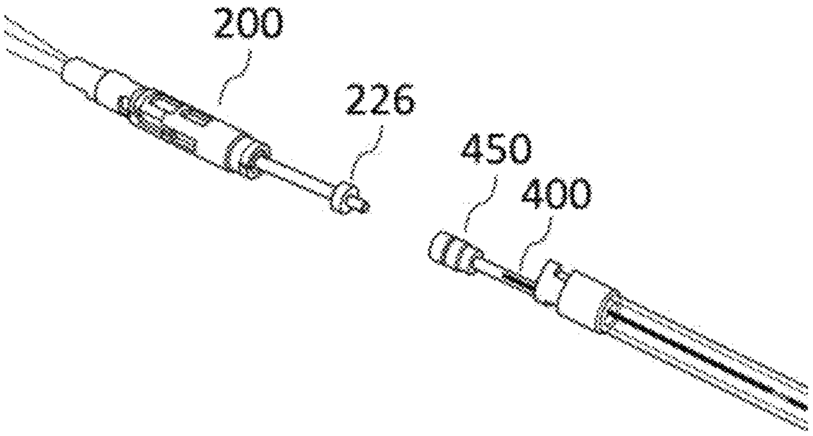
FIGS. 28A to 28C illustrate an alternative method for connecting the lumen expansion device in accordance with the present embodiments to a manipulation rod by using magnetic attraction.
Figure 28B:
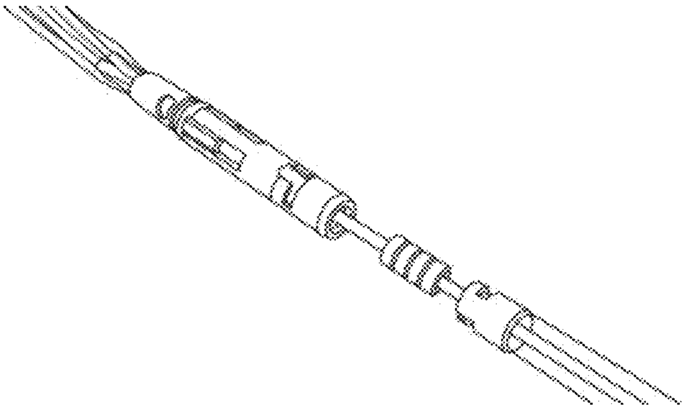
Figure 28C:
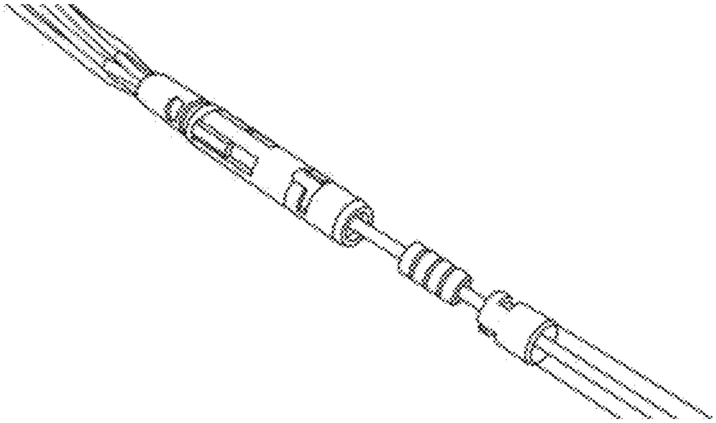

FIGS. 28A to 28C illustrate steps in an alternative method in accordance with the present embodiments for the rejoining process of FIG. 12 where preparation of the retraction of the device uses magnetic attraction. In accordance with this method, a permanent magnet 226 may be attached to the proximal end of the actuation and lock mechanism 200 instead of the U-hook loop. Additionally, a corresponding permanent magnet 450 may be attached to the end of the manipulation rod 400, where the permanent magnet 226 and the corresponding permanent magnet 450 are in different poles such that the magnets 226, 450 attract one another. In this manner, magnetic attraction can advantageously be used to properly orient and engage the actuation and lock mechanism 200 and the manipulation rod 400 for retraction and removal of the device.

Figure 29A:
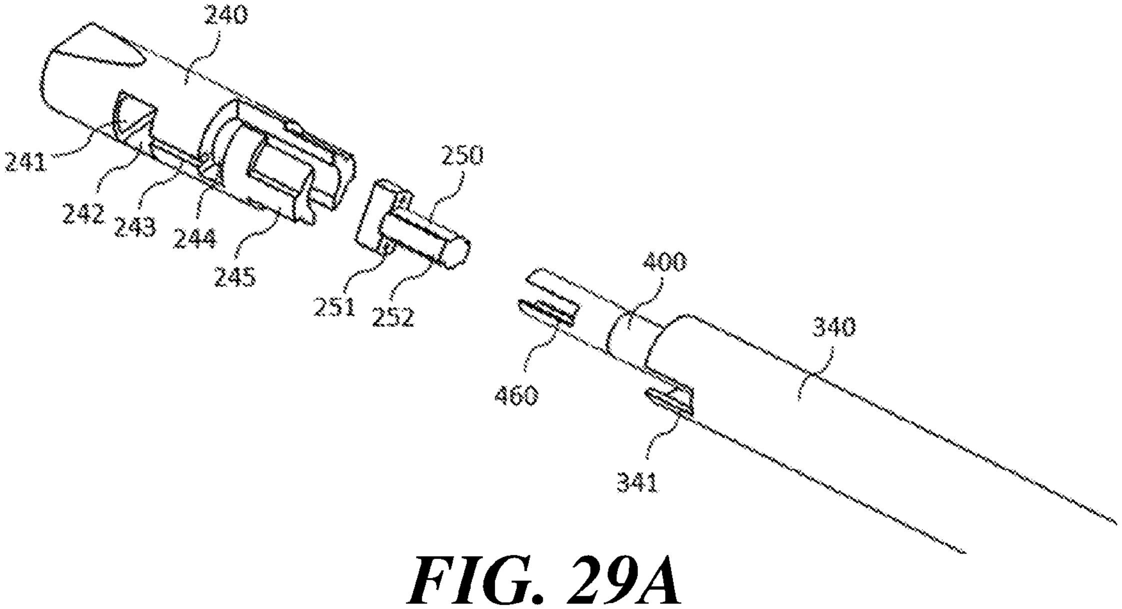
FIG. 29A is an exploded view of another embodiment of an actuation and lock mechanism for the lumen expansion device in accordance with the present embodiments.
Figure 29B:
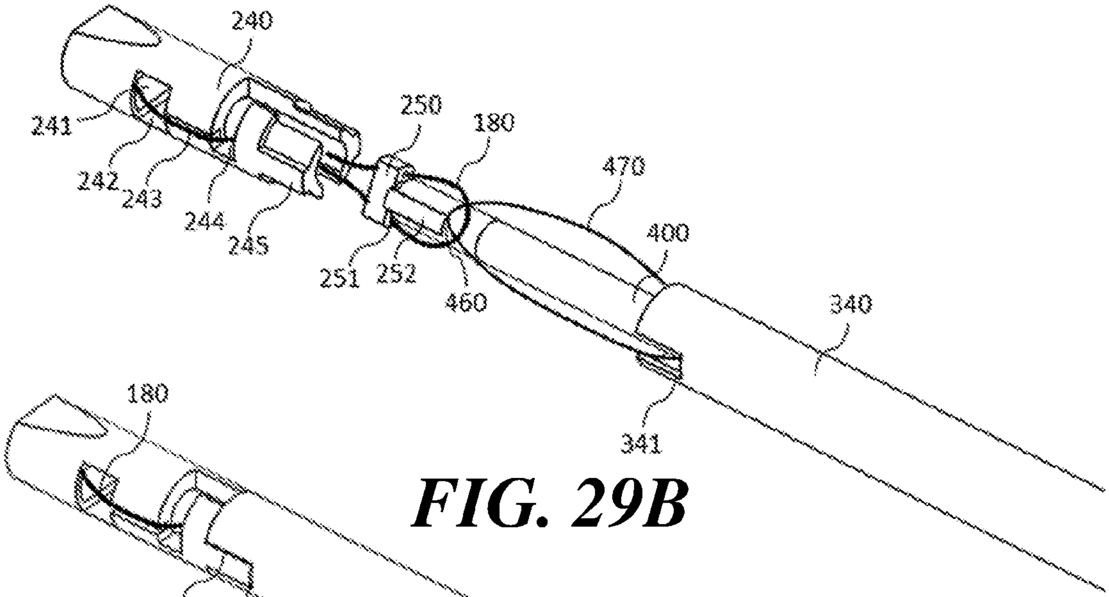
FIG. 29B is an exploded view of the actuation and lock mechanism of FIG. 29A with an actuation line and tensioning line in accordance with the present embodiments.
Figure 29C:
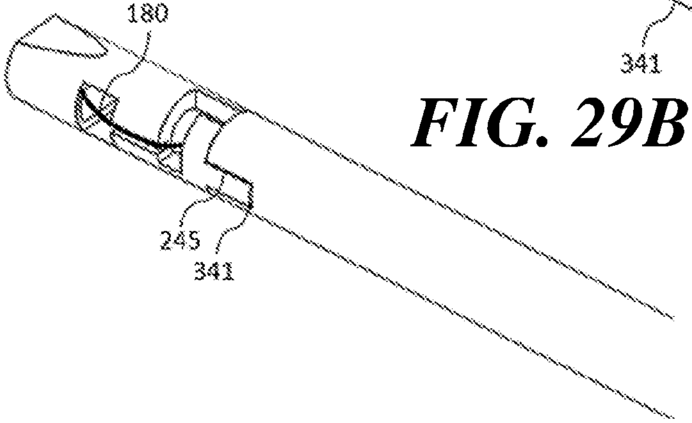
FIG. 29C is a perspective view of the actuation and lock mechanism of FIG. 29A in a closed coupled arrangement in accordance with the present embodiments.

FIGS. 29A to 29C illustrate another embodiment of the actuation and lock mechanism 210 in accordance with a variation of the present embodiments. The actuation and lock mechanism 210 in accordance with this variation comprises two parts, an L-socket actuation base 240 and a T-shaped lock 250. The delivery and manipulation are provided by the manipulation rod 400 and the outer manipulation tube 340. The female connector of the manipulation rod 460 joins with the male connector of the T-shaped lock 252 while a tensioning line 470 facilitates pulling of the actuation line 180 for in situ deployment of the 3D structure. Also, the female connector of the outer manipulation tube 341 connects with the male connector of the L-socket actuation base 245. The actuation line 180 comes in through a middle hole 241, goes out from window 242, routes outside the channel 243, and enters to the inside from the L-socket 244. The actuation line then goes through hole 251 on the T-shaped lock 250.

Figure 30A:
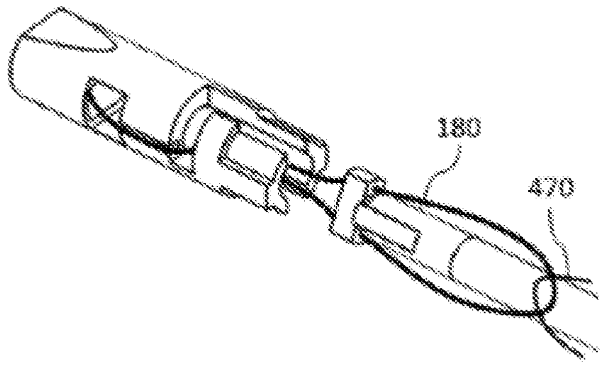
FIGS. 30A to 30D illustrate a tensioning, locking, and detaching sequence for the embodiment of the actuation and lock mechanism of FIGS. 29A to 29C for the lumen expansion device in accordance with the present embodiments.
Figure 30B:
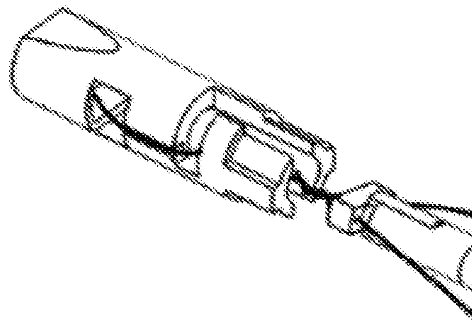
Figure 30C:
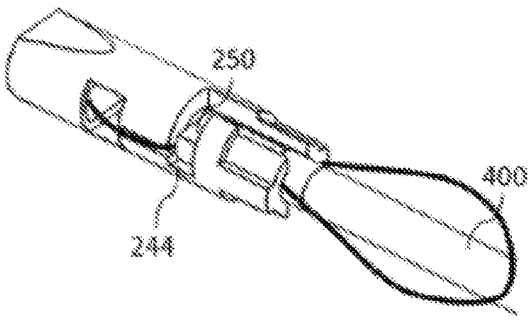
Figure 30D:
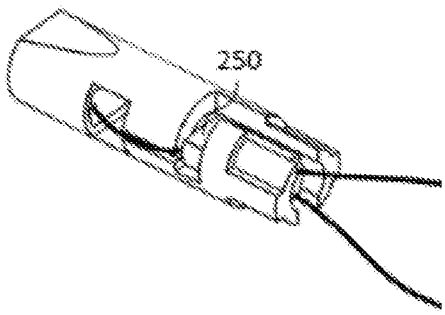

FIGS. 30A to 30D illustrate steps in a tensioning, locking, and detaching process of the variation of the actuation and lock mechanism of FIGS. 29A to 29C. Referring to FIG. 30A, the tensioning line 470 is pulled to tension the actuation line 180. In FIG. 30B, the actuation line 180 is then twisted by rotating the manipulation rod 400. The twisted actuation line 180 provides friction to hold the tension applied. Referring next to FIG. 30C, the T-shaped lock 250 is inserted into the L-socket 244 to prevent the untwisting of the actuation line 180, where the T-shaped locked 250 is coupled to the manipulation rod 400. Then, in FIG. 30D, the manipulation rod 400 is pulled and retracted, leaving the T-shaped lock 250 inserted in the L-socket 244. The rotation of the device is then advantageously prevented by the outer manipulation tube 340 engaged to the L-socket actuation base 240.

Alternatively, the manipulation tools may be in any form as long as the flexible main structure 100 and the actuation and lock mechanism 210 are manipulated as intended. For example, the manipulation tools can consist of flexible tubes and rods with sockets, slots, or hooks at their distal ends.

The present embodiments advantageously provide a device and method for expanding a body lumen or soft collapsible conduit to expose and maintain a workspace such as creating a volume within sidewall tissue of a lumen for endoscopic diagnosis, therapy, and surgery without relying on insufflation. Further, the device may be attached to a general endoscope without increasing the dimensions and used perforation. Further, the device and method in accordance with the present embodiments provides an expanded and stable intra-luminal space for proper visualization of a target area (e.g., target tissue) as well as surrounding sidewalls and creation of a volume within a soft collapsible conduit for a proper workspace to manipulate the delivery mechanism (e.g., an endoscope or catheter or similar flexible assembly) as well as tools or other instruments independently.

While exemplary embodiments have been presented in the foregoing detailed description of the present embodiments, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing exemplary embodiments of the invention, it being understood that various changes may be made in the function and arrangement of steps and method of operation described in the exemplary embodiments without departing from the scope of the invention as set forth in the appended claims.

What is claimed is:

1. A device to provide a three-dimensional volume at a workspace in a body lumen comprising:

a plurality of flexible tube linkages, each one of the plurality of flexible tube linkages having a distal end and a proximal end; and an actuation and locking mechanism comprising an actuation line, an actuation base having a threaded hole, an actuation rod having a screw portion and a lock key, said screw portion arranged to engage the threaded hole, and a locking cap having a key slot, said key slot arranged to engage the lock key to place the actuation and locking mechanism in a locking position;

wherein the proximal end of each of the plurality of flexible tube linkages is coupled to the actuation and locking mechanism, wherein a distal end of the actuation line is connected to the distal ends of each of the plurality of flexible tube linkages, and wherein the actuation and locking mechanism is arranged to rotate relative to the plurality of flexible tube linkages to pull the distal end of the actuation line towards the actuation and locking mechanism thereby moving the distal end of each of the flexible tube linkages towards the proximal end of each of the flexible tube linkages thereby converting the plurality of flexible tube linkages from a closed collapsible structure for transportation to the workplace to a three-dimensional structure defined by the plurality of flexible tube linkages to define the three-dimensional volume at the workspace in the body lumen.

2. The device according to claim 1, wherein the actuation and locking mechanism further comprises a structure wire, said structure wire being perpendicularly connected to the plurality of flexible tube linkages when the defined three-dimensional structure is created.

3. The device according to claim 2, wherein when the actuation and locking mechanism is rotated, tension in said structure wire increases to provide rigidity to the three-dimensional structure defined by the flexible tube linkages.

4. The device according to claim 1, wherein the actuation and locking mechanism comprises a guiding tube, said guiding tube being arranged to provide a passageway for the actuation line.

5. The device according to claim 1, wherein the device further comprises a distal tube coupled to at least one of the plurality of flexible tube linkages, and wherein the actuation line is arranged to pass through the distal tube.

6. The device according to claim 2, wherein the structure wire is arranged to pass through the actuation rod, and wherein the actuation line is arranged to pass through an outer surface of the actuation base.

7. The device according to claim 1, further comprising one or more tissue block lines, said one or more tissue block lines being arranged in relation to the plurality of flexible tube linkages to prevent surrounding tissue at a target site from entering the defined three-dimensional volume in the body lumen.

8. The device according to claim 1, further comprising a manipulation tube having a manipulation rod, said manipulation rod comprising a hook arranged to engage with the actuation and locking mechanism.

9. The device according to claim 8, wherein the manipulation rod is configured to rotate the actuation and locking mechanism.

10. The device according to claim 1, wherein each of the plurality of flexible tube linkages comprises a plurality of linkage portions and rotating elements, wherein each rotating element connects adjoining ones of the plurality of linkage portions.

11. The device according to claim 1, wherein the device is configured to define the three-dimensional volume in the body lumen for an endoscopic procedure, and wherein the defined three-dimensional volume is a hollow shaped rectangular volume arranged to allow an endoscope to pass through.

12. A method for providing a three-dimensional volume in a body lumen, the method comprising the steps of:

advancing a device according to claim 1 to a target site within the body lumen; and rotating the actuation and locking mechanism such that the distal ends of the plurality of flexible tube linkages are brought in close proximity to the proximal ends of the plurality of flexible tube linkages, thereby forming the defined three-dimensional volume in the body lumen, wherein rotating the actuation and locking mechanism comprises attaching a manipulation tube to the actuation and locking mechanism and rotating a manipulation rod to rotate the actuation and locking mechanism.

* * * * *